(12) United States Patent
Bhargava et al.

(10) Patent No.: US 8,593,630 B2
(45) Date of Patent: Nov. 26, 2013

(54) DISCRETE FREQUENCY SPECTROSCOPY AND INSTRUMENTATION

(75) Inventors: Rohit Bhargava, Urbana, IL (US); Brian T. Cunningham, Champaign, IL (US)

(73) Assignee: The Board of Trustees of the University of Illinois, Urbana, IL (US)

(*) Notice: Subject to any disclaimer, the term of this patent is extended or adjusted under 35 U.S.C. 154(b) by 245 days.

(21) Appl. No.: 12/900,172

(22) Filed: Oct. 7, 2010

(65) Prior Publication Data

US 2011/0080581 A1   Apr. 7, 2011

Related U.S. Application Data

(60) Provisional application No. 61/249,303, filed on Oct. 7, 2009.

(51) Int. Cl.
*G01J 3/40* (2006.01)
(52) U.S. Cl.
USPC .......................................... 356/302; 356/326
(58) Field of Classification Search
USPC .................................. 356/300, 302, 326, 445
See application file for complete search history.

(56) References Cited

U.S. PATENT DOCUMENTS

| | | | |
|---|---|---|---|
| 4,009,993 A | 3/1977 | Marazzi et al. | |
| 4,297,579 A * | 10/1981 | Spaeth | 250/343 |
| 4,536,608 A | 8/1985 | Sheng et al. | |
| 4,876,208 A | 10/1989 | Gustafson et al. | |
| 4,931,384 A | 6/1990 | Layton et al. | |
| 4,992,385 A | 2/1991 | Godfrey | |
| 5,216,680 A | 6/1993 | Magnusson et al. | |
| 5,726,805 A * | 3/1998 | Kaushik et al. | 359/589 |
| 5,738,825 A | 4/1998 | Rudigier et al. | |
| 6,507,747 B1 | 1/2003 | Gowda et al. | |
| 6,784,428 B2 | 8/2004 | Rabolt et al. | |
| 6,943,353 B2 | 9/2005 | Elmore et al. | |
| 7,070,987 B2 | 7/2006 | Cunningham et al. | |
| 7,145,722 B2 | 12/2006 | Dutta | |
| 7,167,615 B1 | 1/2007 | Wawro et al. | |
| 7,262,856 B2 | 8/2007 | Hobbs et al. | |
| 7,292,336 B2 | 11/2007 | Cunningham et al. | |
| 7,298,477 B1 | 11/2007 | Cunningham et al. | |

(Continued)

FOREIGN PATENT DOCUMENTS

| | | |
|---|---|---|
| WO | WO 97/44686 | 5/1997 |
| WO | WO 2008/069454 | 6/2008 |
| WO | WO 2009/050437 | 4/2009 |
| WO | WO 2009/075473 | 6/2009 |

OTHER PUBLICATIONS

Yen, Gary Jef (2006) "New Applications for Guided Mode Resonance Filters," Thesis, Master of Science in Electrical and Computer Engineering, University of Illinois, Urban-Champaign.

(Continued)

*Primary Examiner* — Layla Lauchman
(74) *Attorney, Agent, or Firm* — Lathrop & Gage LLP

(57) ABSTRACT

Described herein are spectrometers comprising one or more wavelength-selective filters, such as guided mode resonance filters. Some of the spectrometers described herein are configured for obtaining absorbance spectra in a discrete fashion by measuring absorbances of a sample at multiple discrete wavelengths or wavelength bands. In another aspect, methods are also provided for obtaining spectra, images and chemical maps of samples in a discrete fashion.

32 Claims, 12 Drawing Sheets

(56) References Cited

U.S. PATENT DOCUMENTS

| | | | |
|---|---|---|---|
| 7,300,803 | B2 | 11/2007 | Lin et al. |
| 7,301,628 | B2 | 11/2007 | Cunningham et al. |
| 7,327,454 | B2 | 2/2008 | Cunningham et al. |
| 7,330,614 | B1 | 2/2008 | Mossberg et al. |
| 7,371,562 | B2 | 5/2008 | Cunningham et al. |
| 7,400,399 | B2 | 7/2008 | Wawro et al. |
| 7,420,673 | B2 * | 9/2008 | Hagler ............ 356/310 |
| 7,422,891 | B2 | 9/2008 | Cunningham et al. |
| 7,429,492 | B2 | 9/2008 | Lin et al. |
| 7,430,044 | B2 * | 9/2008 | Hagler ............ 356/310 |
| 7,435,385 | B2 | 10/2008 | Lin et al. |
| 7,436,500 | B2 * | 10/2008 | Treado et al. .......... 356/73 |
| 7,479,404 | B2 | 1/2009 | Cunningham et al. |
| 7,656,523 | B2 * | 2/2010 | Sun et al. ............. 356/301 |
| 7,944,557 | B2 * | 5/2011 | Hagler ............ 356/310 |
| 2002/0127565 | A1 | 9/2002 | Cunningham et al. |
| 2003/0027327 | A1 | 2/2003 | Cunningham et al. |
| 2003/0027328 | A1 | 2/2003 | Cunningham et al. |
| 2005/0025422 | A1 | 2/2005 | Magnusson et al. |
| 2006/0193550 | A1 | 8/2006 | Wawro et al. |

OTHER PUBLICATIONS

Alaiya et al. (Web Release Jun. 24, 2005) "Clinical Cancer Proteomics: Promises and Pitfalls" *J. Proteome Res.* 4:1213-1222.

Alivisatos (Jan. 2004) "The use of nanocrystals in biological detection" *Nat. Biotechnol.* 22(1):47-52.

Andrus (2006) "Cancer monitoring by FTIR spectroscopy" *Tech. Cancer Res. Treat.* 5:157-167.

Argov (Apr. 2002) "Diagnostic potential of Fourier-transform infrared micro-spectroscopy and advanced computational methods in colon cancer patients" *J. Biomed. Opt.* 7(2):248-254.

Astratov et al. (Nov. 1999) "Resonant Coupling of Near-Infrared Radiation to Photonic Band Structure Waveguides," *J. Lightwave Technol.* 17(11):2050-2057.

Bertoni et al (Jan. 1989) "Frequency selective reflection and transmission by a periodic dielectric layer" *IEEE Trans. Antennas Propag.* 37(1):78-83.

Bhargava et al. (Nov. 1, 2001) "Fourier transform infrared imaging: theory and practice," *Anal Chem* 73:5157-5167.

Bhargava et al. (Mar. 15, 2002) "Effective time averaging of multiplexed measurements: a critical analysis," *Anal Chem* 74:1429-1435.

Bhargava et al. (2008) "Infrared Spectroscopic Imaging Protocols for High-Throughput Histopathology," In; *Vibrational Spectroscopy for Medical Diagnosis*, Diem et al. Eds., Wiley, pp. 155-186.

Bhargava et al. (Web Release May 17, 2006) "High throughput assessment of cells and tissues: Bayesian classification of spectral metrics from infrared vibrational spectroscopic imaging data." *Biochim Biophys Acta.* 1758(7): 830-845.

Bhargava et al. (2001) "Theory and application of gain ranging to Fourier transform infrared spectroscopic imaging." *Appl. Spectrosc.* 55(12):1580-1589.

Bhargava et al. (2003) "Time-resolved Fourier transform infrared spectroscopic imaging." *Appl. Spectrosc.* 57(4):357-366.

Bhargava et al. (2001) "Novel route to faster Fourier transform infrared spectroscopic imaging." *Appl. Spectrosc.* 55(8):1079-1084.

Bhargava et al. (2003) "FTIR microspectroscopy of polymeric systems." *Adv. Polym. Sci.* 163:137-191.

Bhargava et al. (2000) "Route to higher fidelity FT-IR imaging." *Appl. Spectrosc.* 54(4): 486-495.

Bhargava et al. (2008) "Towards a Practical Fourier Transform Infrared Chemical Imaging Protocol for Cancer Histopathology," *Anal Bioanal Chem.* 389:1155-1169.

Block et al. (Mar. 2008) "A sensitivity model for predicting photonic crystal biosensor performance" *IEEE Sensors Journal* 8(3):274-280.

Boonruang et al. (2006) "Multiline two-dimensional guided-mode resonant filters," *Appl. Opt.* 45:5740-5747.

Boroditsky et al. (Aug. 23, 1999) "Light extraction from optically pumped light-emitting diode by thin-slab photonic crystals" *Appl. Phys. Lett.* 75(8):1036-1038.

Boroditsky et al. (Nov. 1999) "Spontaneous Emission Extraction and Purcell Enhancement from Thin-Film 2-D Photonic Crystals" *J. Lightwave Technol.*17(11):2096-2112.

Boydston-White et al. (1999) "Infrared Spectroscopy of Human Tissue. V. Infrared Spectroscopic Studies of Myeloid Leukemia (ML-1) Cells at Different Phases of the Cell Cycle" *Biospectroscopy* 5: 219-227.

Braue et al. (1987) "Consistency in circle cell FT-IR analysis of aqueous solutions" *Appl. Spectrosc.* 41(6):1057-1067.

Carr et al. (2005) "Multichannel Detection with a Synchrotron Light Source: Design and Potential," In; *Spectrochemical Analysis Using Infrared Multichannel Detector*, Bhargava et al. Ed., Blackwell Publishing 56-84.

Chan et al. (Web Release Aug. 1, 2008) "Raman spectroscopy and microscopy of individual cells and cellular components" *Laser and Photonics Reviews* 2(5):325-349.

Charlton et al. (Web Release Jun. 9, 2005) "Infrared Evanescent field sensing with quantum cascade lasers and planar silver halide waveguides" *Analytical Chemistry* 77(14):4398-4403.

Cheng et al. (Jul. 2002) "Laser-scanning coherent anti-Stokes Raman scattering microscopy and applications to cell biology" *Biophys. J.* 83:502-509.

Christiansen et al. (1953) "A culture chamber for the continuous biochemical and morphological study of living cells in tissue culture" *Experimental Cell Research* 5:10-15.

Cohenford et al. (Dec. 1998) "Cytologically normal cells from neoplastic cervical samples display extensive structural abnormalities on IR spectroscopy: Implications for tumor biology" *PNAS* 95:15327-15332.

Colarusso et al. (1998) "Infrared spectroscopic imaging: From planetary to cellular systems" *Appl. Spectrosc.* 52(3):106a-120a.

Conrads (2003) "Cancer diagnosis using proteomic patterns" *Expert Rev. Mol. Diagn.* 3:411-420.

Cunningham et al. (2002) "A plastic colorimetric resonant optical biosensor for multiparallel detection of label-free biochemical interactions," *Sensors and Actuators B* 85:219-226.

Cunningham et al. (2002) "Colorimetric resonant reflection as a direct biochemical assay technique" *Sensors and Actuators B* 81:316-328.

Diem et al. (Oct. 2004) "A decade of vibrational micro-spectroscopy of human cells and tissue" *Analyst* 129(10):880-885.

Diem et al. (2002) "IR spectra and IR spectral maps of individual normal and cancerous cells" *Biopolymers Biospectroscopy* 67:349-353.

Dobbs et al. (2006) "Fabrication of a graded-wavelength guided-mode resonance filter photonic crystal" *Appl. Phys. Lett.* 89: 123113.

Dobbs et al. (Oct. 1, 2006) "Optically tunable photonic crystal reflectance filters," *Applied Optics.* 45(28):7286-7293.

Edwards et al. (2003) "Advantage of the Mark-III FEL for biophysical research and biomedical applications" *Journal of Synchrotron Radiation* 10:354-357.

Ellis et al. (2006) "Metabolic fingerprinting in disease diagnosis: biomedical applications of infrared and Raman spectroscopy" *Analyst* 131:875-885.

Erchak et al. (Jan. 29, 2001) "Enhanced coupling to vertical radiation using a two-dimensional photonic crystal in a semiconductor light-emitting diode" *Appl. Phys. Lett.* 78(5):563-565.

Fabian et al. (1995) "A comparative infrared spectroscopic study of human breast tumors and breast tumor cell xenografts" *Biospectroscopy* 1:37-45.

Fan et al. (2002) "Analysis of guided resonances in photonic crystal slabs," *Phys. Rev. B* 65: 235112-1-235112-8.

Fernandez et al. (Apr. 2005) "Infrared spectroscopic imaging for histopathologic recognition" *Nat Biotechnol.* 23(4):469-474.

Ganesh et al. (2006) "Near UV-wavelength photonic crystal biosensor with enhanced surface-to-bulk sensitivity ratio," *Applied Physics Letters* 89: 023901-023904.

Goodpaster et al. (2008) "An immunohistochemical method for identifying fibroblasts in formalin-fixed, paraffin-embedded tissue" *J. Histochem. Cytochem.* 56: 347-58.

Griffiths et al. (1986) "Data Systems," "Disperse Fourier Transform Spectrometry," "FT-IR Spectrometry of Time-Dependent Phenomena," "FT-IR Studies of Polymers," "Biochemical and Biomedical

(56) References Cited

OTHER PUBLICATIONS

Applications," and "Low-Temperature Studies," In; *Fourier Transform Infrared Spectrometry* ($2^{nd}$ edn), John Wiley & Sons: New York, USA Ch. 6, 11, 12, 13, 14, 15, pp. 220-247 and 369-519.
Haaland et al. (1997) "Multivariate classification of the infrared spectra of cell and tissue samples" *Appl. Spectrosc.* 51(3):340-345.
Hake et al. (May 2000) "Uncooled Barium Strontium Titanium Focal Plane Array Detection for Mid-Infrared Fourier Transform Spectroscopic Imaging" *Appl Spectrosc* 54(5):753-755.
Hessel et al. (Oct. 1965) "A new theory of Wood's anomalies on optical gratings," *Appl. Opt.* 4(10):1275-1297.
Holman et al. (2003) "Tracking chemical changes in a live cell: Biomedical applications of ST-FTIR spectromicroscopy" *Spectroscopy* 17:139-159.
Holst, G.C., (1998) "Infrared Imaging System Operation," and "General Measuring Techniques," In; *Testing and Evaluation of Infrared Imaging Systems* ($2^{nd}$ edn), Copublished by JCD Publishing and SPIE Optical Engineering Press: Bellingham, WA, USA; Chapters 2 and 4.
Huffman et al. (2002) "Generalized implementation of rapid-scan Fourier transform infrared spectroscopic imaging." *Appl. Spectrosc.* 56(8):965-969.
Hvozdara et al. (2002) "Quantum cascade lasers for mid-infrared spectroscopy" *Vibrational Spectroscopy* 30:53-58.
Jackson (2004) "From Biomolecules to biodiagnostics: Spectroscopy does it all," *Faraday Discuss.* 126:1-18.
Jackson et al. (1995) "Beware of connective tissue proteins: Assignment and implications of collagen absorptions in infrared spectra of human tissues" *Biochimica et Biophysica Acta* 1270:1-6.
Jackson et al. (1999) "Classification of Breast Tumors by Grade and Steroid Receptor Status Using Pattern Recognition Analysis of Infrared Spectra" *Cancer Det. Prevent.* 23(3): 245-253.
Kano et al. (Feb. 21, 2005) "Vibrationally resonant imaging of a single living cell by supercontinuum-based multiplex coherent anti-Stokes Raman scattering microspectroscopy" *Opt. Exp.* 13(4):1322-1327.
Keith et al. (2008) "Practical protocols for fast histopathology by Fourier transform Infrared spectroscopic imaging" *Proc. of SPIE* 6853:685306.
Kobayashi et al. (2005) "Surface laser emission from solid polymer dye in a guided mode resonant grating filter structure" *Appl. Phys. Lett.* 87:151106.
Koenig et al. (Jul. 1, 2001) "FT-IR Images" *Anal. Chem.* 73:361A-369A.
Krafft et al. (2009) "Disease recognition by infrared and Raman spectroscopy" *J. Biophotonics* 2(1-2):13-28.
Kuimova et al. (2009) "Chemical imaging of live cancer cells in the natural aqueous environment" *Appl. Spectrosc.* 63(2):164-171.
Lasch et al. (2002) "Spatially resolved IR microspectroscopy of single cells" *Biopolymers—Biospectroscopy* 67:335-338.
Levin et al. (2005) "Fourier transform infrared vibrational spectroscopic imaging: integrating microscopy and molecular recognition," *Ann. Rev Phys Chem.* 56:429-474.
Lewis et. al. (Oct. 1, 1995) "Fourier transform spectroscopic imaging using an infrared focal-plane array detector," *Anal Chem* 67:3377-3381.
Magnusson et al. (1992) "New principle for optical filters," *Appl. Phys. Lett* 61:1022-1024.
Moss et al (Web Release Jun. 8, 2005) "IR microspectroscopy of live cells" *Vibrational Spectroscopy* 38(1-2):185-191.
National Research Council (US) (2006)Committee on Revealing Chemistry through Advanced Chemical Imaging, National Research Council *Visualizing Chemistry: The Progress and Promise of Advanced Chemical Imaging*, National Academies Press.
Naumann (2001) "FT-Infrared and FT-Raman Spectroscopy in Biomedical Research" *Appl. Spectrosc. Rev.* 36(2-3):239-298.

Olumi et al. (Oct. 1, 1999) "Carcinoma-associated fibroblasts direct tumor progression of initiated human prostatic epithelium," *Cancer Res.* 59:5002-5011.
Peng et al. (Apr. 15, 1996) "Experimental demonstration of resonant anomalies in diffraction from two-dimensional gratings," *Opt. Lett.* 21(8):549-551.
Peng et al. (May 1996) "Resonant scattering from two-dimensional gratings," *J Opt. Soc. Am. A* 13(5):993-1005.
Popov et al. (1986) "Theoretical study of the anomalies of coated dielectric gratings," *Opt. Acta* 33:607-619.
Puppels et al. (Sep. 20, 1990) "Studying single living cells and chromosomes by confocal Raman microspectroscopy" *Nature* 347:301-303.
Ransohoff (2002) "Challenges and opportunities in evaluating diagnostic tests" *J Clin Epidemiol.* 55:1178-1182.
Ransohoff et al. (Apr. 2004) "Rules of evidence for cancer molecular-marker discovery and validation" *Nature Reviews Cancer* 4:309-314.
Ransohoff et al. (2008) "The process to discover and develop biomarkers for cancer: A work in progress" *Journal of the National Cancer Institute* 100:1419-1420.
Rayleigh (1907) "On the dynamical theory of gratings," *Proc. R. Soc. London Ser.* A 79:399-416.
Rosenberg et al. (Aug. 22, 2005) "Guided resonances in asymmetrical GaN photonic crystal slabs observed in the visible spectrum," *Opt. Express* 13(17):6564-6571.
Simon et al. (Jan. 1, 2003) "Pitfalls in the use of DNA microarray data for diagnostic and prognostic classification" *J Natl Cancer Inst.* 95(1):14-18.
Snively et al. (Dec. 15, 1999) "Fourier-transform infrared imaging using a rapid-scan spectrometer" *Opt. Lett.* 24(24):1841-1843.
Srinivasan et al (Jul. 1, 2007) "Fourier transform-infrared spectroscopic imaging: The emerging evolution from a microscopy tool to a cancer imaging modality" *Spectroscopy* 22(7).
Suh et al. (Jan. 14, 2004) "All-pass transmission or flattop reflection filters using a single photonic crystal slab," *Appl. Phys. Lett.* 84(24):4905-4907.
Swain et al. (2007) "Raman Microspectroscopy for non-invasive biochemical analysis of single cells" *Biochemical Society Transactions* 35(3):544-549.
Timlin et al. (2008) "Dynamics of cellular activation as revealed by attenuated total reflectance infrared spectroscopy" *Vibrational Spectroscopy* 50:78-85.
Uzunbajakava et al. (Jun. 2003) "Nonresonant Confocal Raman imaging of DNA and protein distribution in apoptotic cells" *Biophys. J.* 84:3968-3981.
Volkmer et al. (Feb. 18, 2005) "A Vibrational imaging and microspectroscopies based on coherent anti-stokes raman scattering microscopy" *J. Physics Applied Physics* 38:R59-R81.
Wang et al. (May 10, 1993) "Theory and applications of guided-mode resonance filters," *Appl. Opt.* 32(14):2606-2613.
Wang et al. (Aug. 1990) "Guided-mode resonances in planar dielectric-layer diffraction gratings," *J. Opt. Soc. Am. A* 7(8):1470-1474.
Willets et al. (2009) "Surface-enhanced Raman scattering (SERS) for probing internal cellular structure and dynamics" *Anal Bioanal. Chem.* 394:85-94.
Wood et al. (Apr. 1902) "On a remarkable case of uneven distribution of light in a diffraction grating spectrum," *Philos. Mag.* 4:269-275.
Wood et al. (2004) "Fourier transform infrared (FTIR) spectral mapping of the cervical transformation zone, and dysplastic squamous epithelium" *Gynecologic Oncology* 93(1):59-68.
Wood et al. (1998) "FTIR microspectroscopic study of cell types and potential confounding variables in screening for cervical malignancies" *Biospectroscopy* 4:75-91.
Yang et al. (2007) "A voltage-tuned resonant reflectance optical filter for visible wavelengths fabricated by nanoreplica molding," *Applied Physics Letters* 90: 261109-261111.

* cited by examiner

DISCRETE FREQUENCY SPECTROSCOPY AND INSTRUMENTATION

CROSS REFERENCE TO RELATED APPLICATION

This application claims the benefit of and priority under 35 U.S.C. 119(e) to U.S. Provisional Application 61/249,303 filed on Oct. 7, 2009, which is hereby incorporated by reference in its entirety.

STATEMENT REGARDING FEDERALLY SPONSORED RESEARCH OR DEVELOPMENT

This invention was made with government support under R01EB009745 awarded by the National Science Foundation (NIH). The government has certain rights in the invention.

BACKGROUND OF THE INVENTION

This invention is in the field of spectroscopy and spectroscopic imaging. This invention relates generally to devices and methods for obtaining infrared spectra and spectroscopic imaging data in the mid-infrared region.

The collection of spectroscopic (magnetic resonance, mass, infrared and Raman, for example) techniques that can provide imaging data are referred to as chemical imaging and are rapidly evolving for biomedical applications. Molecular spectroscopy-based imaging, including mid-infrared absorption and Raman scattering, is attractive as it can optically probe materials in a non-perturbing manner. Fourier transform IR (FT-IR) spectroscopic imaging, in particular, combines the spatial specificity of optical microscopy with the molecular selectivity of vibrational spectroscopy. Since mid-IR spectral frequencies are resonant with the fundamental vibrational mode frequencies in molecules, the IR absorption is a strong signal and the spectrum at each pixel is a quantitative "fingerprint" of composition. For example, structure in prostate tissue is manually determined after staining in current practice (FIG. 1A). For example, the biochemical content of unstained tissue has been obtained using FT-IR imaging. At each pixel in the image, a vibrational spectrum is recorded to provide a 3D data cube (FIG. 1B). By dialing-in chemistry inherent in IR spectral features (FIG. 1C), contrast similar to stains can be obtained (FIG. 1D). As opposed to human recognition, further, numerical methods can provide information objectively (FIG. 1E) as images that are color coded for cell type, pathologic status or function. Hence, chemical imaging offers the potential for recognition of the type and functional state of tissues and cells without the use of dyes, probes or human interpretation. Automation and objectivity are enabled, further, by the numerical methods needed to extract data. Chemical imaging may be contrasted with molecular imaging. While probe-based molecular imaging techniques are exceptional for monitoring specific epitopes, dyes and reagents are required and functional state of cells and tissues is limited to known pathways that involve the probe target. Chemical imaging, in contrast, requires no probes but uses computation to extract information. While the functional state can be extensively probed and multiple phenomena in multiple cell types can be monitored at the same time, the information is not as specific as that with molecular probes. The flexibility and general applicability, hence, of chemical imaging is very high but is traded-off against information detail—making it suitable for many applications. Among spectroscopic techniques, IR and Raman spectroscopy are attractive in that they can easily harness the power of optics and microscopy while providing richer molecular detail compared to the near-infrared (NIR), visible or ultraviolet regions. The Raman effect is ideally suited for analyzing wet biological materials but, unfortunately, is too weak to provide dynamic details sensitively for large numbers of cells. Nonlinear and surface enhanced Raman spectroscopic methods are emerging to greatly improve sensitivity. The new methods are limited by spectral coverage and understanding the molecular/optical origin of signals in the former while may only be surface sensitive or require probes in the latter. At the same time, it is widely believed that IR spectroscopy cannot be easily conducted in aqueous environments. In summary, the exciting potential of chemical imaging is limited by technology. Hence, vigorous attempts are being made to improve instrumentation/technology in Raman and FT-IR spectroscopic imaging.

For example, International Patent Application Publication No. WO 2009/050437 discloses a system and method for infrared imaging and use of a broadband infrared source with one or more high efficiency infrared band-pass filters. Additionally, U.S. Pat. No. 6,784,428 discloses an apparatus and method for non-interferometric IR spectroscopy using an optically dispersive element.

SUMMARY OF THE INVENTION

Described herein are spectrometers. For example, devices useful for obtaining infrared spectra at wavelengths between 2 μm and 12 μm are disclosed. Also described are methods for obtaining infrared spectra in the mid-infrared region using one or more infrared guided mode resonance filters.

In one aspect, described herein are spectrometers and spectroscopic imaging devices. In one embodiment, a spectrometer comprises: a source for generating a beam of electromagnetic radiation; one or more wavelength-selective filters positioned in optical communication with the source; and a detector for detecting electromagnetic radiation, the detector positioned in optical communication with at least one of the one or more wavelength-selective filters. In a specific embodiment, a spectrometer further comprises a sample chamber positioned in optical communication with at least one of the one or more wavelength-selective filters. For example, the sample chamber is positioned in optical communication with the source and/or the detector. In embodiments, the wavelength-selective filters are selected from the group consisting of: a reflective optical filter, a transmissive optical filter, a guided mode resonance filter, a distributed Bragg reflective filter, and any combination of these.

In an exemplary embodiment, at least one of the one or more filters has a reflectance band center position selected over the range of 0.2 μm to 14 μm. In embodiments, a spectrometer is an infrared spectrometer. Infrared spectrometers of some embodiments are advantageous in that they comprise one or more guided mode resonance useful for reflecting electromagnetic radiation in specific regions of the mid-infrared region. In an exemplary embodiment, at least one of the one or more infrared guided mode resonance filters has a reflectance band center position selected over the range of 2 μm to 14 μm, for example selected over the range of 2 μm to 12 μm or any other sub-range or sub-value therein, such as at 1080 $cm^{-1}$, 1456 $cm^{-1}$, 1556 $cm^{-1}$, 1338 $cm^{-1}$ or 1234 $cm^{-1}$, or selected over the range of 900 to 1975 $cm^{-1}$, 1300 to 1358 $cm^{-1}$, 1426 to 1482 $cm^{-1}$, 1070 to 1104 $cm^{-1}$ or 1324 to 1358 $cm^{-1}$.

Useful wavelength-selective filters include those having reflectance linewidths of 2 μm, 4 μm, 16 μm or any reflectance linewidth selected over the range of 2 $cm^{-1}$ to 128 $cm^{-1}$.

Though not required, a preferable filter has a maximum reflectance selected over the range of 10% to 100% or 90% to 100%, for example selected over the range of 95% to 100% or 97% to 99%. A preferred filter embodiment has a reflectance contrast greater than 100, and/or selected over the range of 10 to 1000000.

In a specific embodiment, the one or more wavelength-selective filters are positioned on a filter wheel, the filter wheel configured to position one wavelength-selective filter at a time in optical communication with the source. In a specific embodiment, each wavelength-selective filter on a filter wheel has a different reflectance band center position. In an exemplary embodiments, the one or more filters are sequentially positioned in optical communication with the source. Optionally, one or more optical elements may be present in optical communication with the source, such as a polarizer, a mirror, an aperture, a lens, a prism, a window, a filter and any combination of these or other optical elements useful for directing or otherwise manipulating a beam of electromagnetic radiation. The one or more optical elements are useful in some embodiments, for example, for directing electromagnetic radiation between the source and a filter, a filter and a sample, and/or a sample and a detector.

Detectors useful with the spectrometers and methods described herein include two-dimensional detectors. In a specific embodiment, a spectrometer is an imaging spectrometer and the detector is a two-dimensional detector and/or an array detector. In a specific embodiment, the detector is a cooled detector, a focal plane array detector and/or a cooled focal plane array detector.

Wavelength-selective filters useful with the spectrometers and methods described herein include guided mode resonance filters fabricated for reflecting electromagnetic radiation. Optionally, least one of the wavelength-selective filters comprises a multilayered structure that is spatially varying in one or more dimensions. In embodiments, a guided mode resonance filter comprises: a substrate having a first index of refraction; and a dielectric layer having a second index of refraction disposed over at least a portion of the substrate, wherein the dielectric layer has a periodic thickness. In specific embodiments, the dielectric layer has a periodicity selected over the range of 1000 nm to 6000 nm, for example selected over the range of 1000 to 2000 nm, 2000 to 3000 nm, 3000 to 4000 nm, 4000 to 5000 nm or 5000 to 6000 nm. Preferably, the dielectric layer has a periodicity configured for reflecting a specific wavelength of electromagnetic radiation. In specific embodiments, the dielectric layer has a first thickness selected over the range of 100 nm to 500 nm and a second thickness selected over the range of 200 nm to 1000 nm, for example where the first thickness. Preferably, the thickness of the dielectric layer is configured for reflecting a specific wavelength of infrared electromagnetic radiation.

For some embodiments, the substrate comprises an infrared electromagnetic radiation absorbing material. Useful substrates include, but are not limited to, substrates comprising soda lime glass, silicon, germanium and any combination of these or other microfabrication substrates. For certain embodiments, the dielectric layer comprises a material which does not substantially absorb infrared electromagnetic radiation. Useful dielectric layers include, but are not limited to, dielectric layers comprising silicon nitride. Silicon nitride is useful as it is a material which does not absorb significantly in the mid-infrared region.

In another aspect, provided are methods for measuring an electromagnetic spectral response of a sample. A method of this aspect comprises the steps of: generating a beam of electromagnetic radiation; directing the beam of electromagnetic radiation onto one or more wavelength-selective filters, thereby generating a beam of filtered electromagnetic radiation; directing the beam of filtered electromagnetic radiation through a sample, thereby exposing the sample to filtered electromagnetic radiation; and detecting filtered electromagnetic radiation which interacts with the sample. In an embodiment, the filtered electromagnetic radiation which interacts with the sample is filtered electromagnetic radiation which passes through the sample.

In yet another aspect, provided are methods for measuring an electromagnetic spectral image. A method of this aspect comprises the steps of: generating a beam of electromagnetic radiation; directing the beam of electromagnetic radiation onto one or more wavelength-selective filters, thereby generating a beam of filtered electromagnetic radiation; directing the beam of filtered electromagnetic radiation into a microscope, wherein the microscope focuses the filtered electromagnetic radiation; providing a sample in the microscope thereby exposing the sample to focused filtered electromagnetic radiation; and imaging the focused filtered electromagnetic radiation onto a two dimensional detector.

Another method of this aspect comprises the steps of: generating a beam of electromagnetic radiation; directing the beam of electromagnetic radiation into a microscope, wherein the microscope focuses the electromagnetic radiation; providing a sample in the microscope, thereby exposing the sample to focused electromagnetic radiation; directing the beam of focused electromagnetic radiation onto one or more wavelength-selective filters, thereby generating filtered electromagnetic radiation; and imaging the filtered electromagnetic radiation onto a two dimensional detector.

In a specific method of this latter aspect, comprises the steps of: generating a beam of infrared electromagnetic radiation; directing the beam of infrared electromagnetic radiation into a microscope positioned, wherein the microscope focuses the infrared radiation to a focus; providing a sample at the focus of the microscope, thereby exposing the sample to focused infrared radiation; directing the beam of focused infrared electromagnetic radiation onto one or more infrared guided mode resonance filters, thereby generating a filtered beam of infrared electromagnetic radiation; and imaging the filtered electromagnetic radiation onto a two dimensional infrared detector.

For each of the above described methods, embodiments are contemplated where the beam of electromagnetic radiation comprises infrared electromagnetic radiation. Embodiments are also contemplated where one or more of the wavelength-selective filters comprise guided mode resonance filters. Embodiments are also contemplated where the two dimensional detector comprises a two dimensional infrared detector.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

DETAILED DESCRIPTION OF THE INVENTION

Figure 1:
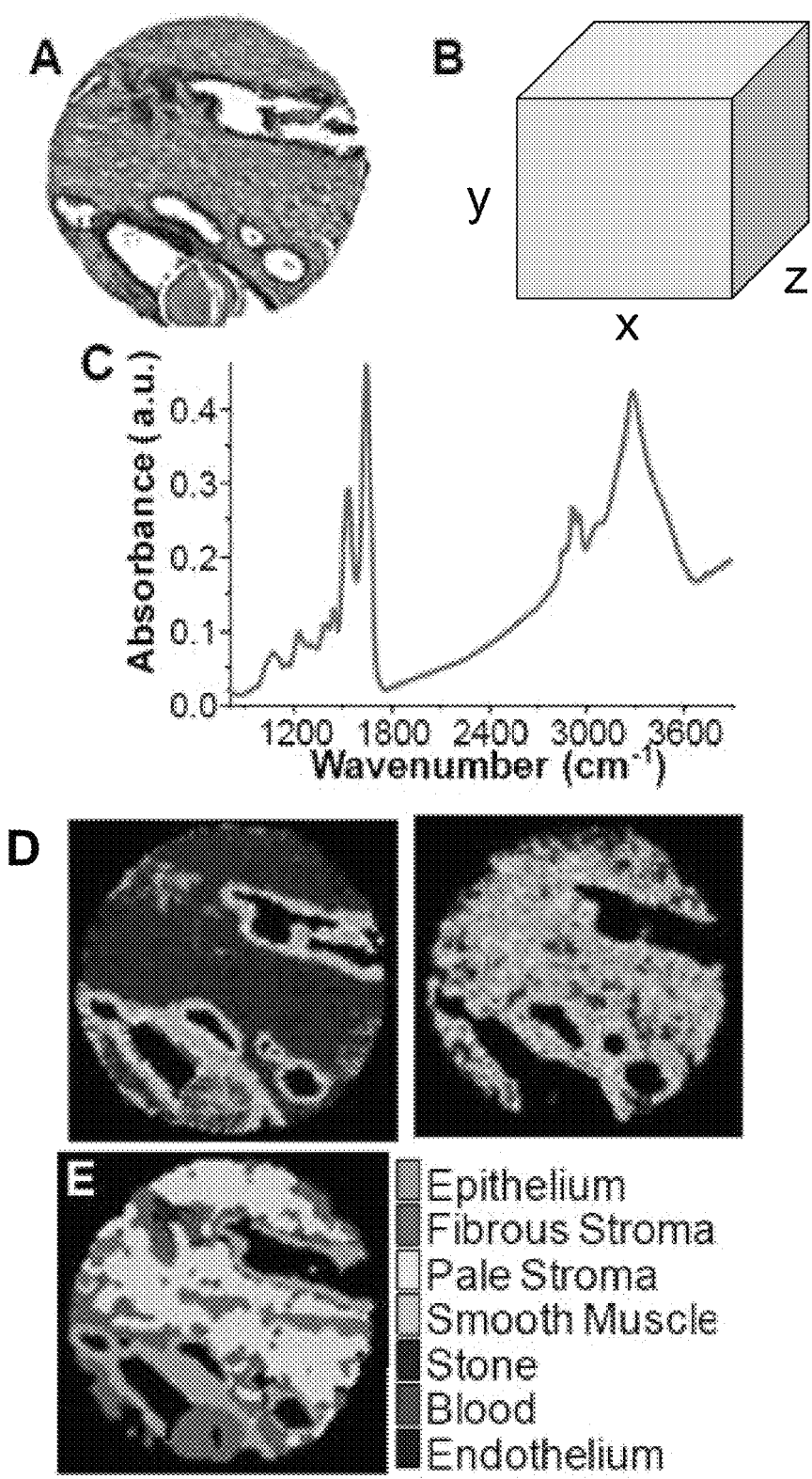
FIG. 1 provides an overview of aspects of spectroscopic imaging including images showing a number of different cell types.

In general the terms and phrases used herein have their art-recognized meaning, which can be found by reference to standard texts, journal references and contexts known to those skilled in the art. The following definitions are provided to clarify their specific use in the context of the invention.

"Optical communication" refers to an orientation of components such that the components are arranged in a manner that allows light or electromagnetic radiation to transfer between the components.

"Guided Mode Resonance Filter" and "GMRF" refer to a reflectance filter configured for reflecting a band of electromagnetic radiation. In some embodiments, a guided mode resonance filter comprises a periodic arrangement of materials having differing indices of refraction. "Infrared Guided Mode Resonance Filter" and "IR GMRF" refer to a Guided Mode Resonance Filter configured for reflection of infrared electromagnetic radiation, for example with reflectivities selected within the range of 50 to 100%. For certain embodiments, the reflectance band of a GMRF is a function of the material properties (e.g., index of refraction) and spatial configuration of the filter components (e.g., periodicity length, layer thicknesses).

"Reflectance" refers to a property of an optical element indicative of the percentage of incident electromagnetic radiation which is reflected by the optical element.

"Reflectance band" refers to a region of the electromagnetic spectrum over which an optical element reflects incident electromagnetic radiation above a particular reflectance threshold. In specific embodiments, a reflectance band is a region of the electromagnetic spectrum over which an optical element reflects more than 0%, more than 1%, more than 5% or more than 10% of incident electromagnetic radiation.

"Reflectance linewidth" and "reflectance band linewidth" refer to a difference between two points of specified reflectance within a reflectance band. In a specific embodiment, a reflectance linewidth is the full width at half maximum (FWHM) of a reflectance band.

"Reflectance center position" and "reflectance band center position" refers to a central wavelength of a reflectance band. In a specific embodiment, the reflectance band center position is the wavelength of a reflectance band with the highest reflectance. In a specific embodiment the reflectance band center position is the wavelength located half way between two points of specified reflectance within a reflectance band.

"Reflectance contrast" and "reflectance band contrast" refers to a property of a reflectance filter equal to the ratio of the reflectance of the reflectance band center position to the reflectance of a wavelength outside of the reflectance band. For some embodiments, the reflectance contrast provides an indication of how strongly a reflectance filter will reflect within its target reflectance band when compared to a position outside its reflectance band.

"Filter wheel" refers to a device comprising multiple filter elements spatially arranged about a point or axis of rotation, for example radially and/or circumferentially.

"Imaging infrared spectrometer" and "infrared imaging spectrometer" refer to a device configured for obtaining infrared spectra of a target area. Some infrared imaging spectrometers are useful for obtaining chemical maps of a sample.

"Absorbance" refers to a measure of the ability of a material to block or otherwise absorb electromagnetic radiation. In one embodiment, the absorbance, A, of a material may be described as a function of the ratio of $I/I_0$, where I is the intensity of electromagnetic radiation after passing through the material and $I_0$ is the intensity of electromagnetic radiation before passing through the material. In some cases, absorbance may be defined as $A=-\log(I/I_0)$. For many materials, absorbance is a function of the wavelength of the electromagnetic radiation. Absorbance need not be a quantitative or absolute measurement, but can instead be a measurement of relative absorption. Absorbance may be normalized to a maximum absorbance value in a given wavelength range or to an absorbance at a specific wavelength.

"Spectrum" refers to a plot of a variable as a function of wavelength, frequency, wavenumber and/or energy; a spectrum can also refer to an array of values or multidimensional distribution of variables as a function of wavelength, frequency, wavenumber and/or energy. "Absorption spectrum" refers to a plot of absorbance as a function of wavelength, frequency, wavenumber and/or energy. An infrared absorption spectrum can be plotted as a function of wavelength, frequency, wavenumber and/or energy of electromagnetic radiation.

"Chemical map" refers to a spatial plot showing spatially resolved variations in chemical composition. In the case of specific identification of component materials, a chemical map can show the relative positions of chemical components within an object.

"Two-dimensional infrared detector" refers to a device configured for detection of infrared electromagnetic radiation over two spatial dimensions. In one embodiment, a two-dimensional infrared detector comprises a plurality of infrared electromagnetic radiation detecting pixels elements spatially arranged as a detection area (e.g., having a detection area with a width and length).

"Focal plane array detector" refers to a two dimensional detector comprising a plurality of electromagnetic radiation detecting elements positioned at the focal plane of a lens.

"Periodic" refers to an object or property that is repeated at regular intervals. "Periodic thickness" refers to the thickness of a layer which varies, the variation being repeated at regular spatial intervals.

"A material which does not substantially absorb infrared electromagnetic radiation" refers to an optical layer, substrate, or material which absorbs only a small amount of incident infrared electromagnetic radiation, for example a material which absorbs less than 40%, less than 30%, less than 20%, less than 10%, less than 5% or less than 1% of incident infrared electromagnetic radiation.

Described herein are infrared spectrometers comprising one or more infrared guided mode resonance filters. Some of the infrared spectrometers described herein are configured for obtaining infrared absorbance spectra in a discrete fashion by measuring infrared absorbances of a sample at multiple discrete wavelengths or wavelength bands. In another aspect, methods are also provided for obtaining infrared spectra, infrared images and chemical maps of samples in a discrete fashion.

Use of infrared guided mode resonance filters provides significant benefits over other contemplated methods of generating filtered or narrow linewidth infrared electromagnetic radiation, including use of tunable infrared laser sources or Fabry-Perot etalons. Use of infrared laser sources requires time consuming and precise alignment; furthermore, infrared laser sources tunable over a broad infrared range and with narrow linewidths, such as would be useful in the mid-infrared range, are not well developed. When broad range infrared laser sources are available, such as free electron lasers, they are prohibitively costly and often not practical for spectroscopic measurements. Although generally tunable, Fabry-Perot devices have a major disadvantage, in that they simultaneously pass multiple bands when used with broad band electromagnetic radiation sources. When used in the mid-infrared region, they furthermore do not provide high enough throughput given the low intensity of mid-infrared optical sources. Infrared guided mode resonance filters overcome the drawbacks of other infrared filtering techniques with the unexpected benefits of high reflectance, narrow linewidths and/or broad wavelength usability range, as guided mode resonance filters in the infrared region were not previously available.

Figure 2:
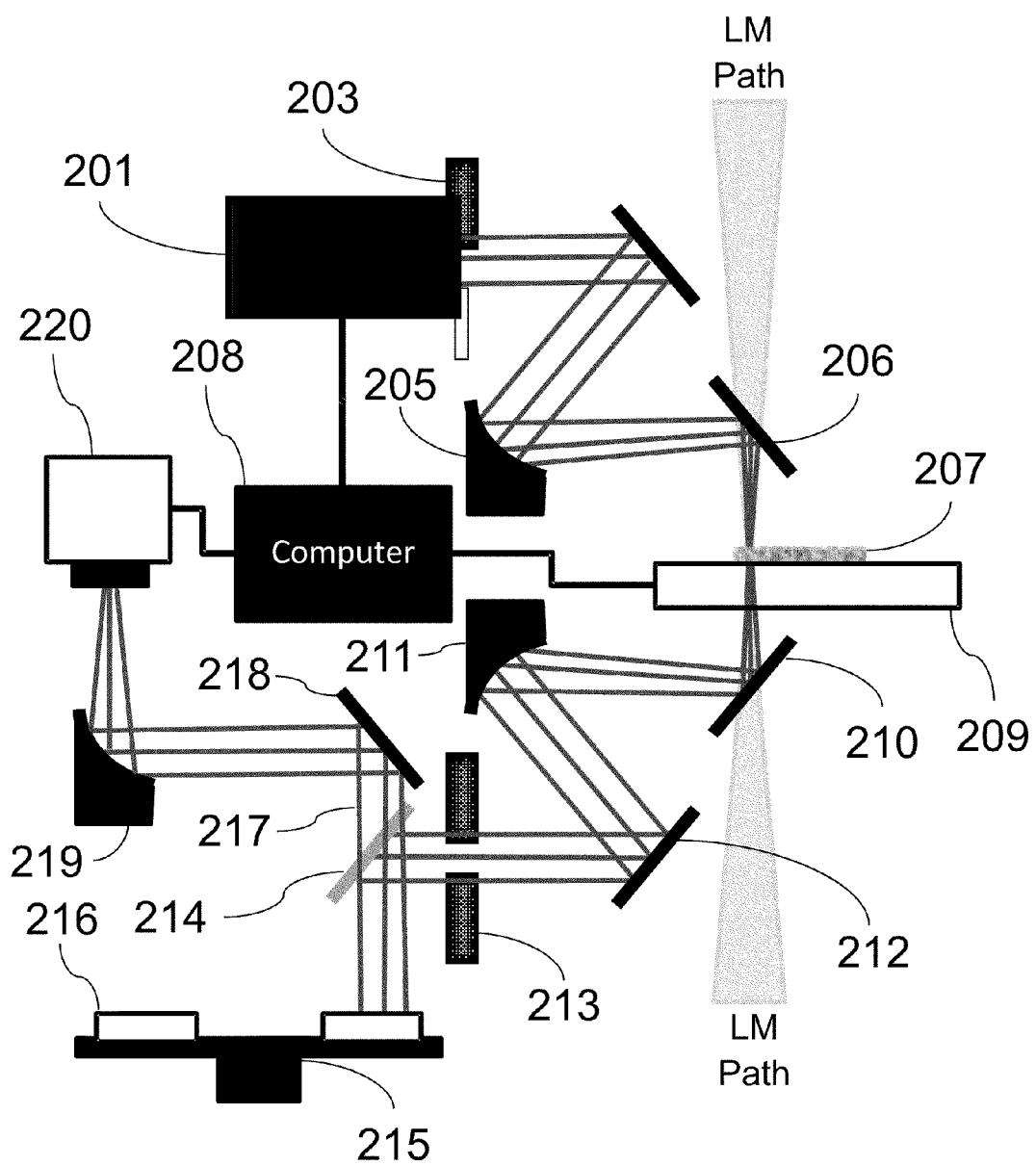
FIG. 2 illustrates an embodiment of an infrared spectroscopic imaging system.

FIG. 2 illustrates an infrared spectroscopic imaging system embodiment. A collimated source 201 generates a beam of broadband infrared electromagnetic radiation 202. A rectangular aperture 203 is optionally provided to shape the beam 202. A broadband mirror 204 reflects beam 202 onto parabolic mirror 205 which focuses beam 202. Another mirror 206 directs beam 202 onto a sample 207. Sample 207 is positioned on a translatable computer 208 controlled microscope stage 209 to allow for positioning of various parts of sample 207 at the focus of beam 202. Another mirror 210 directs beam 202 onto a second parabolic mirror 211 to recollimate beam 202. One additional mirror 212 directs beam 202 through optional entrance slit 213 onto a partially reflecting mirror 214. A portion of beam 202 is directed onto a rotating nanofilter array 215, where GMRFs 216 reflects a filtered infrared beam 217 back towards partially reflecting mirror 214. Filtered beam 217 is directed to mirrors 218 and 219 for redirection and focusing onto array detector 220. Optionally, the positions of source 201 and detector 220 can be switched, such that the beam of broadband infrared electromagnetic radiation 202 reaches nanofilter array 215 and GMRFs 216 before passing through the sample 207.

Figure 3:
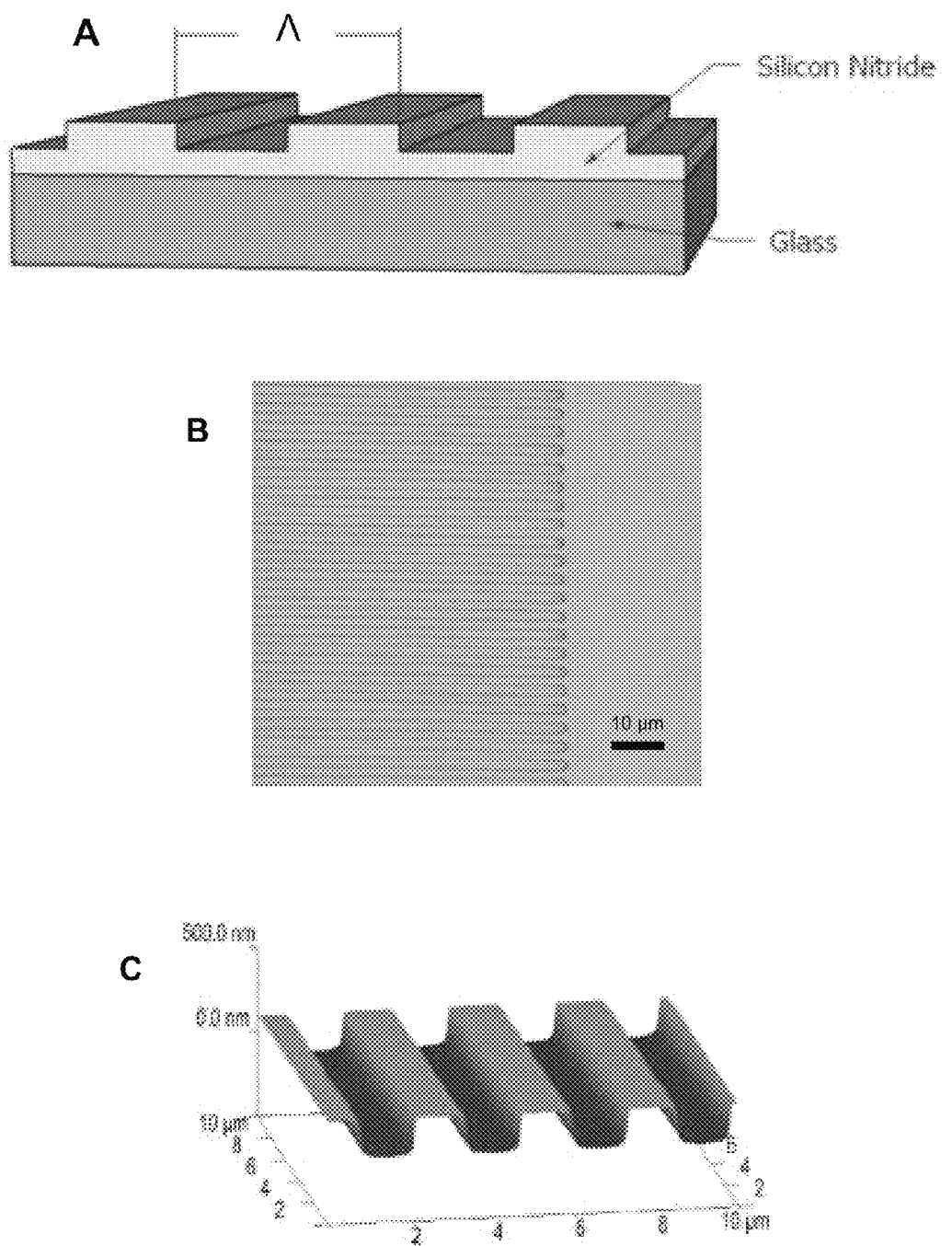
FIG. 3 depicts an exemplary GMRF.

FIG. 3 shows details of a GMRF embodiment. FIG. 3A shows a glass substrate with a Silicon Nitride overlayer. The Silicon Nitride layer has parallel rows of varying thickness with a spacing, Λ, between rows. FIG. 3B depicts a microscope image of the edge of an etched GMRF grating. FIG. 3C depicts an atomic force microscope image of a fabricated GMRF structure showing the grating depth and period.

Figure 4:
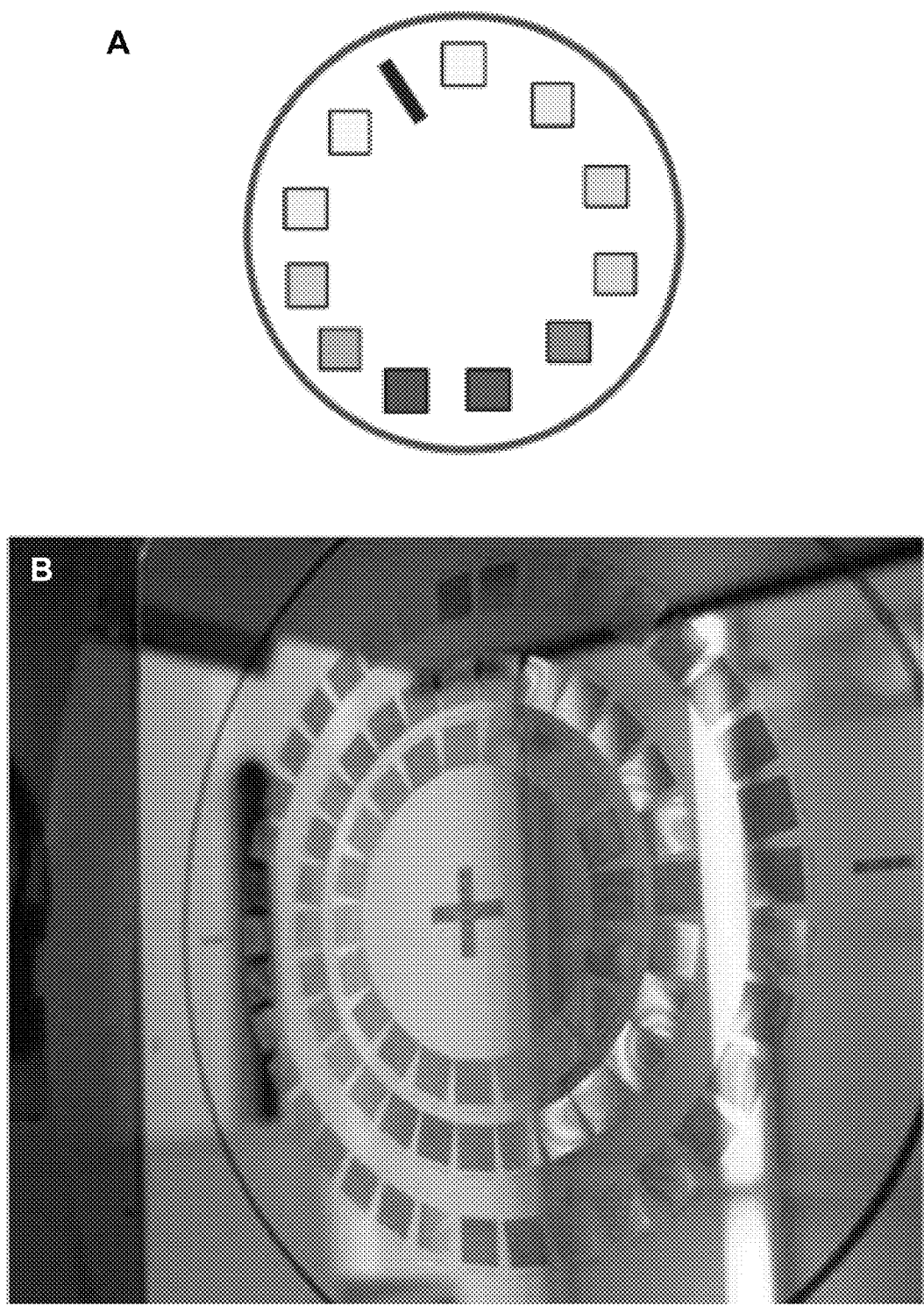
FIG. 4 illustrates a depiction of a filter wheel and an image of a filter wheel.

FIG. 4A illustrates a depiction of a filter wheel. A plurality of guided mode resonance filters are arranged around a ring, with each filter being tuned for reflection of a different portion of the infrared electromagnetic spectrum. A notch is provided as a reference to allow for computer control of rotation of the filter wheel. FIG. 4B depicts a photograph of a filter wheel with three concentric GMRF rings, each having multiple GMRFs.

FIG. 5A provides simulated data showing the reflectance of a single GMRF having a reflectance band at about 3.45 μm, showing a maximum reflectance near 100%. The measured reflectances of four GMRFs, each having a different periodicity, are shown in FIG. 5B. In this embodiment, increasing the periodicity, Λ, results in an increase in the band wavenumber ($cm^{-1}$). FIG. 5C shows an infrared absorbance image of patterned SU-8 polymer obtained using an imaging system similar to that shown in FIG. 2.

Figure 6:
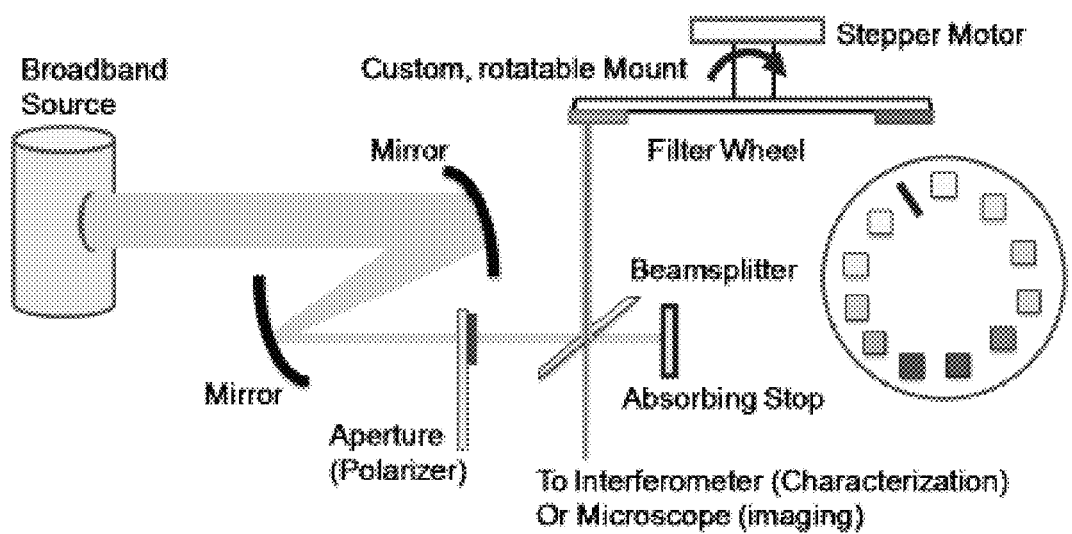
FIG. 6 illustrates a system for filtering a beam of infrared electromagnetic radiation.

In one aspect, existing infrared spectrometers or imaging systems can be adapted to utilize a filter system provided herein. FIG. 6 illustrates an exemplary embodiment of a system comprising a broadband source of infrared electromagnetic radiation which is directed at mirror elements to focus, collimate and/or otherwise reduce the size of the beam of infrared radiation. An aperture and polarizer are positioned in the beam path before the beam interacts with a beam splitter. A portion of the beam is reflected onto a guided mode resonance filter to filter the beam. For certain embodiments, a plurality of guided mode resonance filters are positioned on a filter wheel to allow for selection of any of the guided mode resonance filters to interact with the beam. The filtered beam is then directed to an interferometer or microscope system, for example to allow for characterization or imaging measurements.

Figure 7:
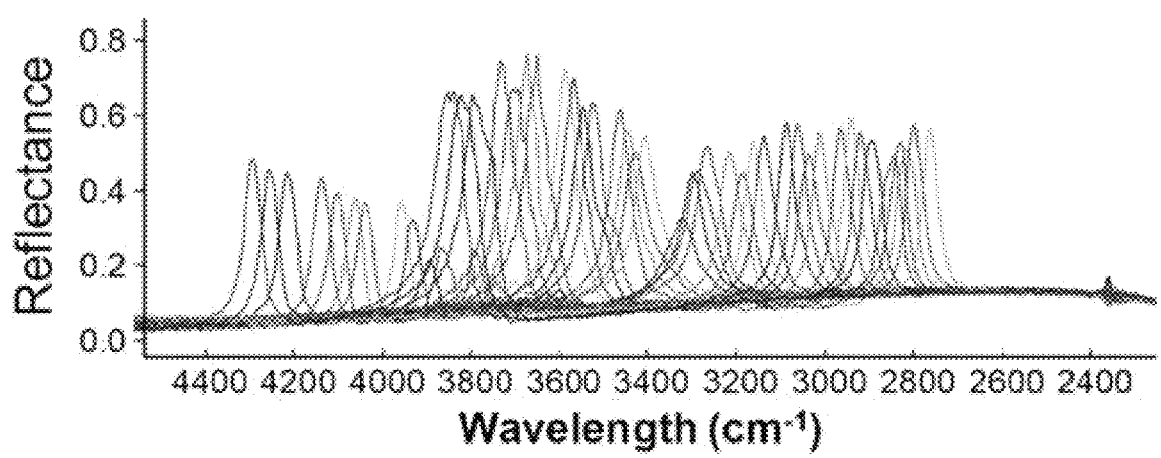
FIG. 7 illustrates reflectance spectra of a large number of guided mode resonance filters.

By providing a plurality of guided mode resonance filters having reflectance bands positioned across the infrared spectral region, infrared spectra can be obtained by performing a number of discrete infrared absorbance measurements. FIG. 7 illustrates reflectance spectra of a large number of guided mode resonance filters, useful for obtaining discrete infrared spectra.

Figure 8:
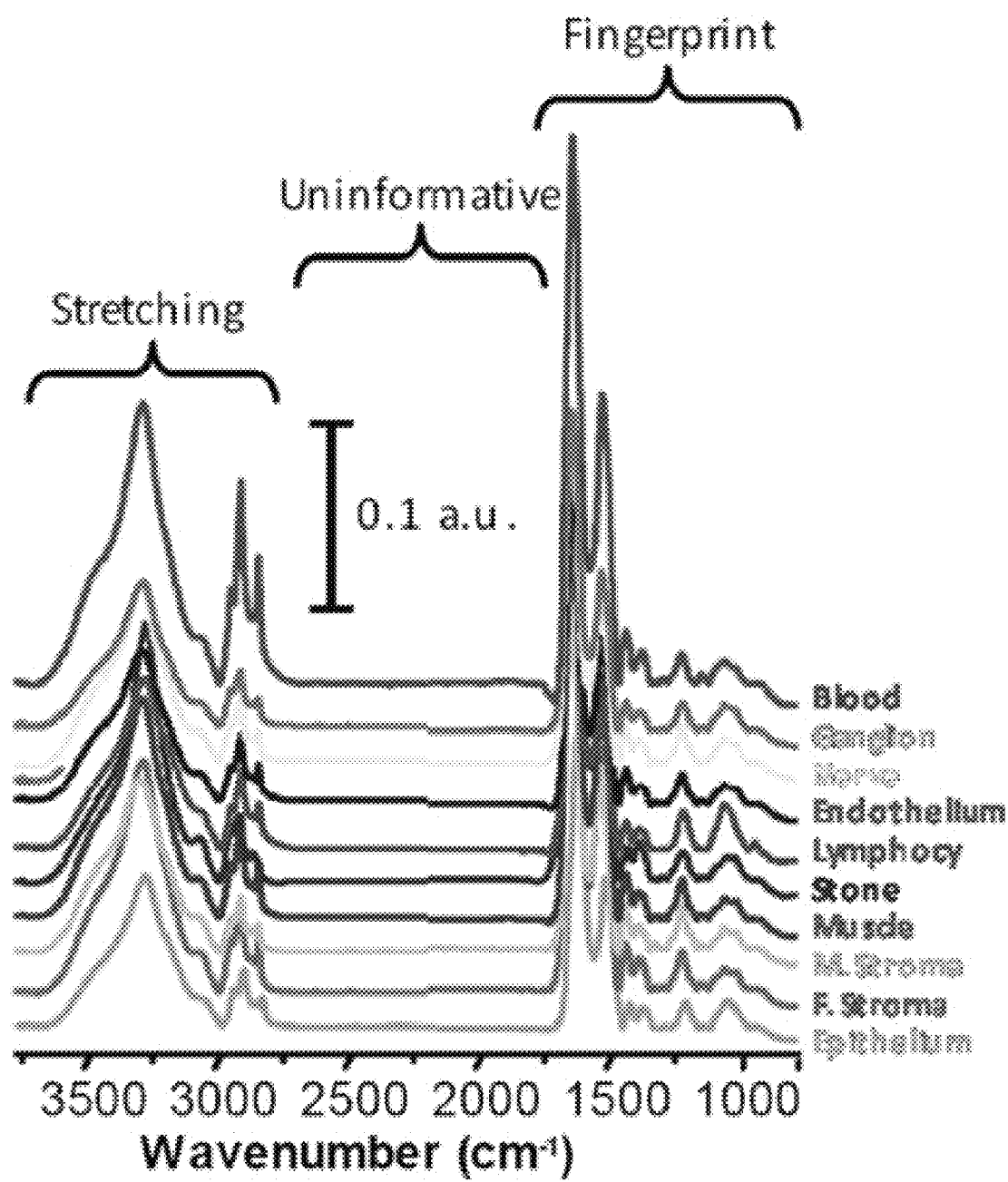
FIG. 8 illustrates infrared absorption spectra for a number of different cell types.
Figure 9:
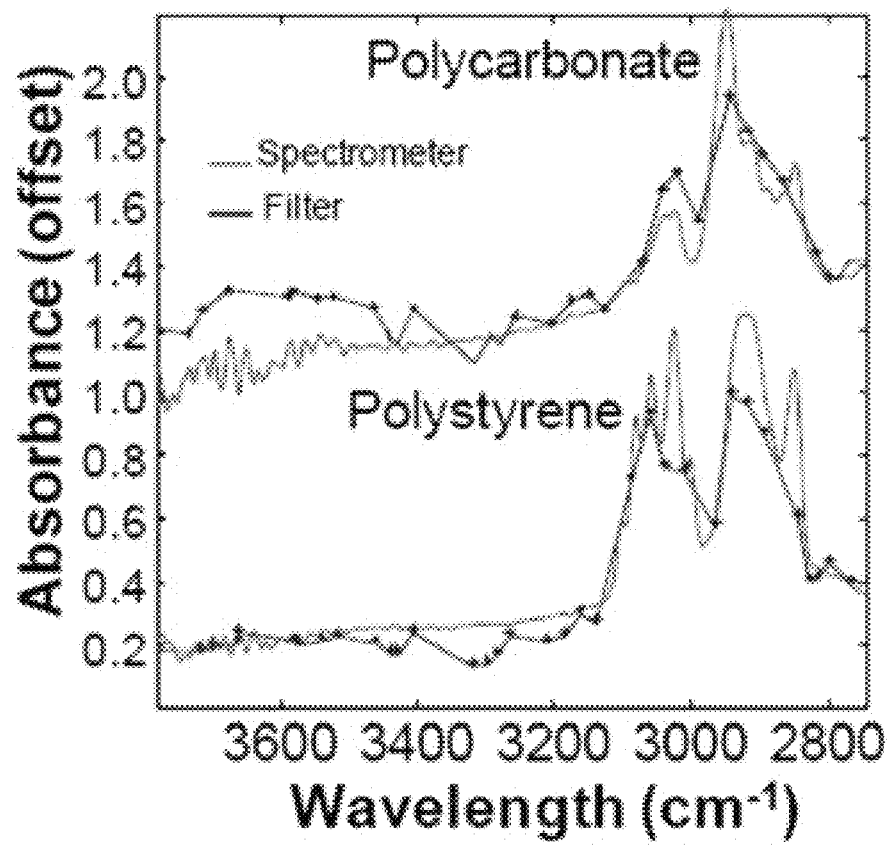
FIG. 9 illustrates absorbance data obtained for polycarbonate and polystyrene.

In one aspect, infrared absorbance measurements can be utilized to distinguish different chemical and or cellular species, as each has a characteristic infrared absorbance spectrum. For example, FIG. 8 illustrates infrared absorption spectra for a number of different cell types. FIG. 9 illustrates comparative absorbance data obtained for polycarbonate and polystyrene. The data shown include those obtained using a spectrometer (for reference) and an infrared spectrometer embodiment utilizing a number of Guided Mode Resonance Filters.

Figure 10:
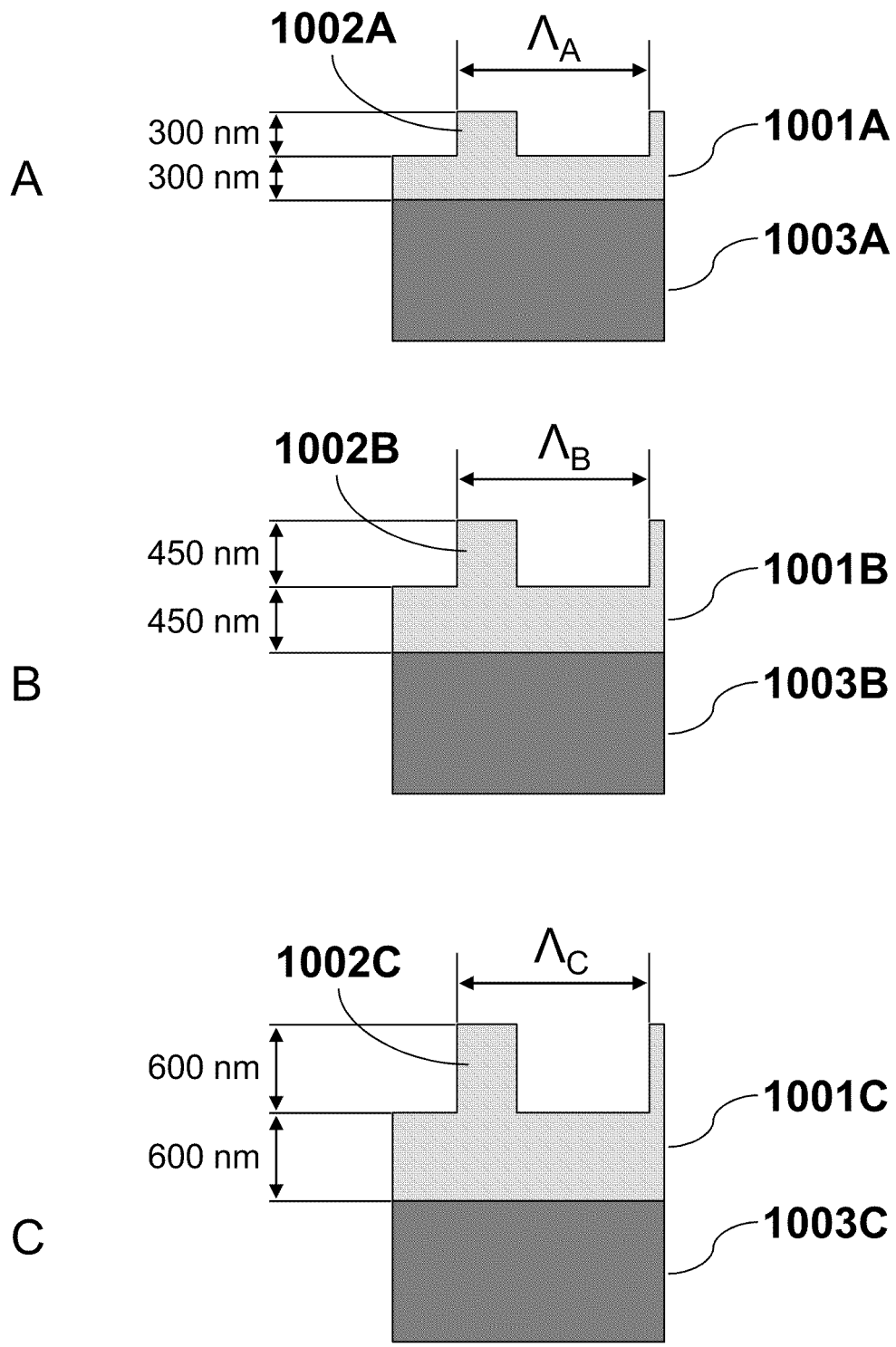
FIG. 10 depicts cross sectional views of three exemplary guided mode resonance filter embodiments.

FIG. 10 depicts cross sectional views of three exemplary guided mode resonance filter embodiments. In FIG. 10A, a 300 nm layer of silicon nitride 1001A having 300 nm features 1002A is present over a glass substrate 1003A. The surface features 1002A are spaced by a periodicity $\Lambda_A$. By adjusting the periodicity, this guided mode resonance filter can be used to reflect infrared radiation selected within the wavelengths of 2.5 to 5.0 μm.

In FIG. 10B, a 450 nm layer of silicon nitride 1001B having 450 nm features 1002B is present over a glass substrate 1003B. The surface features 1002B are spaced by a periodicity $\Lambda_B$. By adjusting the periodicity, this guided mode resonance filter can be used to reflect infrared radiation selected within the wavelengths of 5.0 to 7.5 μm.

In FIG. 10C, a 600 nm layer of silicon nitride 1001C having 600 nm features 1002C is present over a glass substrate 1003C. The surface features 1002C are spaced by a periodicity $\Lambda_C$. By adjusting the periodicity, this guided mode resonance filter can be used to reflect infrared radiation selected within the wavelengths of 7.5 to 10.0 μm.

Figure 11:
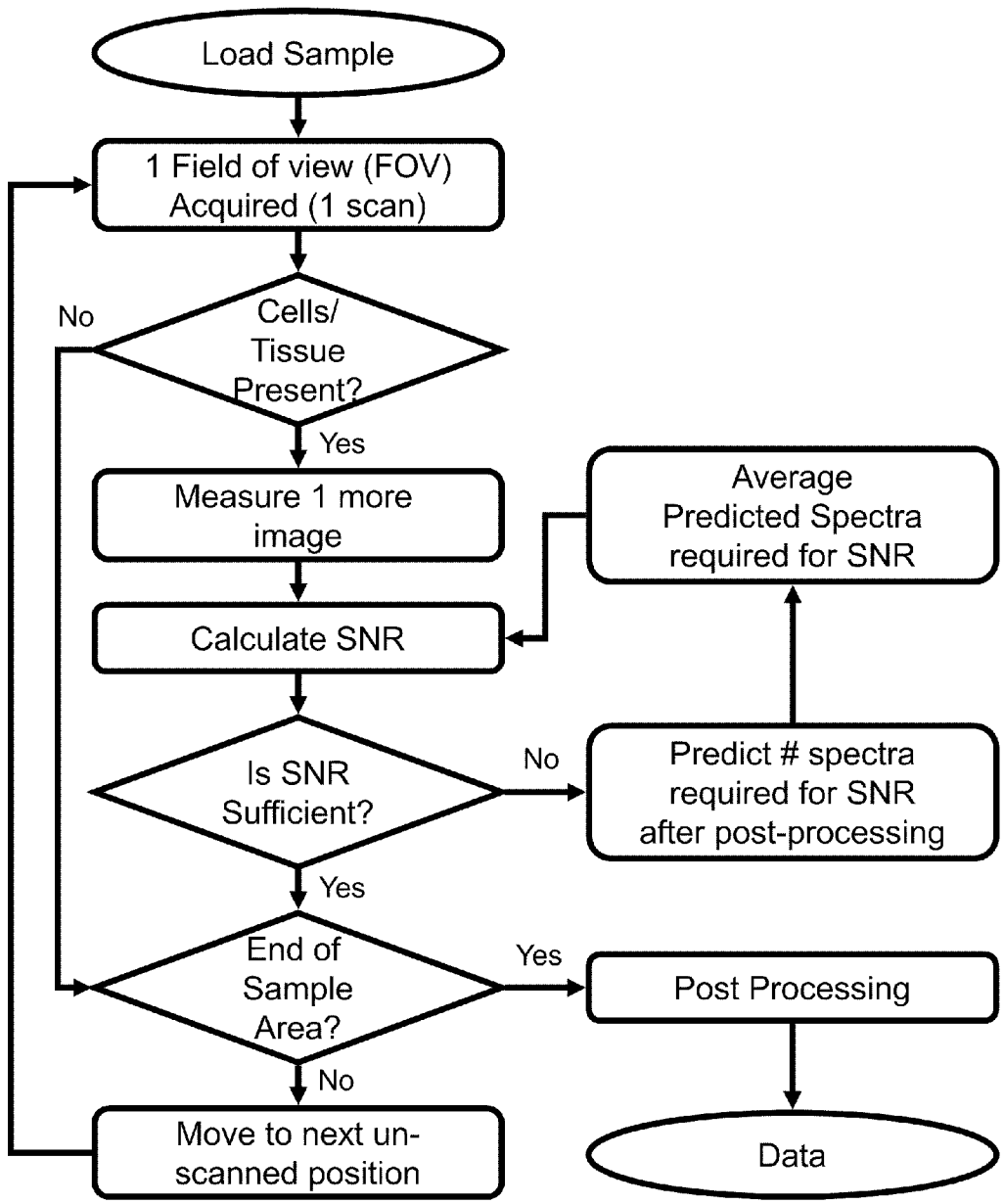
FIG. 11 depicts an overview of an exemplary method for obtaining infrared absorbance images.

FIG. 11 depicts an overview of an exemplary method for obtaining infrared absorbance images. A sample is loaded into an infrared imaging system. A first image is obtained which is analyzed to determine if cells or tissue or the target sample is present. If they are present another image is obtained. The signal to noise ratio (SNR) is determined for the measured images and compared to a threshold SNR. If the SNR is not sufficient, the number of spectra required to meet the SNR after post-processing is calculated and then that number of spectra are obtained. If the SNR is sufficient and the end of the sample area has been reached, then the spectra undergo post-processing. If the end of the sample area has not been reached, the imaging system moves to the next un-scanned position of the sample for additional imaging.

Figure 12:
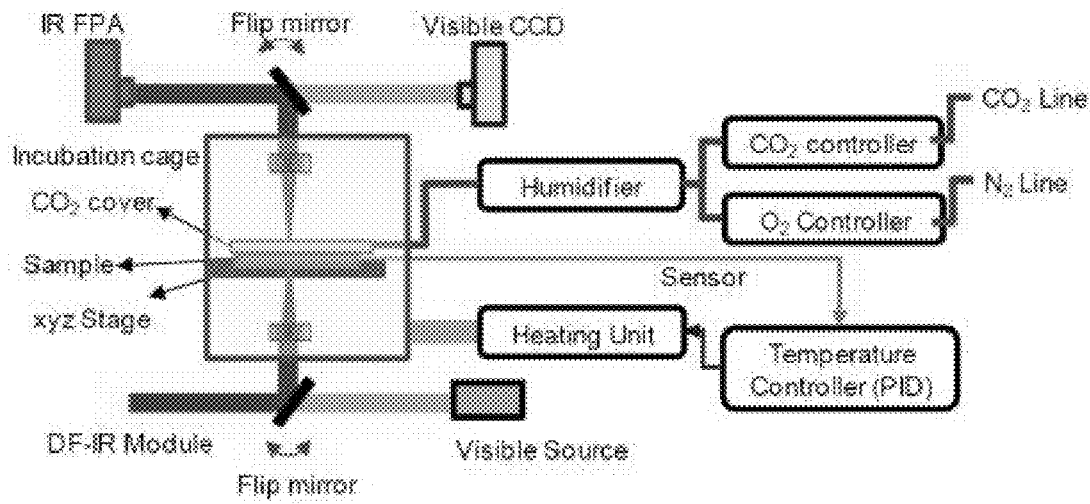
FIG. 12 illustrates a system for infrared and visible imaging measurements.
Figure 13:
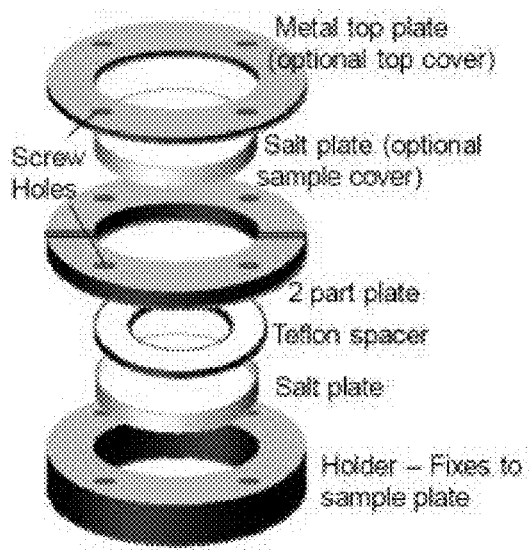
FIG. 13 illustrates an exemplary sample holder embodiment.

FIG. 12 illustrates a system for infrared and visible imaging measurements. By arranging the infrared and visible sources and detectors in such a manner, systems for visible and infrared imaging can switch between visible and infrared operation by simply flipping the positions of two mirrors. FIG. 13 illustrates an exemplary sample holder embodiment for the system of FIG. 12.

The invention may be further understood by the following non-limiting examples.

EXAMPLE 1

Discrete Frequency Infrared Spectroscopy

This example describes novel instrumentation and associated analytical methods for mid-infrared (IR) spectroscopy and imaging. Frequencies in the mid-IR spectral region (wavelength=2-14 µm) are resonant with molecular vibrational frequencies. Hence, the region is widely used for molecular spectroscopy to identify molecules in analytical laboratories, perform structural analysis that determines properties and is an emerging tool for cancer detection and diagnosis. IR spectroscopic imaging combines the molecular selectivity of IR vibrational spectroscopy with the spatial specificity of optical microscopy. Each pixel in an IR spectrum image contains the entire molecular record of the sample via its absorption spectrum. Hence, automated data analysis methods can be used to mine the spectrum for chemical information that relates structure to function.

This example focuses attention on cancer diagnosis as an example of an application. Histopathology is the gold standard of clinical diagnosis and the basis of much research in human cancer. Histologic recognitions, however, are almost exclusively based on human evaluation of tissue morphology. The process is sub-optimal; leading to issues of low throughput, errors in diagnoses and lack of precision in evaluating function or prognosis. Consequently, molecular techniques are increasingly being used to aid pathology, leading to the emergence of the field of molecular pathology in which recognition is aided by chemical characteristics of tissue. One technique that can potentially aid in molecular pathology is mid-IR spectroscopic imaging. Recent laboratory studies have shown that this approach can match human performance and can provide automated disease recognition with accuracy adequate for clinical utility. Translation to the clinic of these exciting results, however, is limited by technology. Specifically, IR spectroscopic imaging instruments are legacy systems that have evolved over 50 years to be general-purpose machines. The lack of high-end performance for tissue imaging, cost, cumbersome nonuser-friendly operation, and limited spatial resolution capability are key barriers that have limited this technique only to expert spectroscopists.

Currently, the dominant technology for IR imaging is Fourier transform infrared (FT-IR) spectroscopic imaging. The technology is accepted widely for use in materials science, forensics and biomedical laboratory measurements. The technology has some shortcomings, however, that make alternative technologies desirable.

Critical barriers in FT-IR imaging. 1. The speed of scanning a specified area (e.g. a glass slide) is impractical. With current commercial technology, imaging a 1 cm×1 cm area would require over 50 hrs. A practical scanning speed would involve imaging a glass slide in <30 minutes.

2. FT-IR imaging technology is cumbersome, requiring an interferometer and an all-reflecting IR microscope (since glass absorbs mid-IR light in the fingerprint region). Conventional glass slides cannot be used for the same reason. A compact instrument, which is robust and easy to operate would be more useful and would be truly compatible with research/clinical practice if it could use standard glass slides.

3. Examination of wet samples is impossible due to strong water absorption in transmission or reflection mode. Hence, "real-time" pathology is not possible, for example, in a surgical venue.

4. The spatial resolution of transmission imaging is diffraction limited. Spectral wavelengths being long (2.5-11 µm), spatial resolution is relatively poor (~equal to wavelength). The lack of spatial delineation is especially problematic in quantifying morphologic parameters for small foci of cells separated from each other by a thin layer of another cell type (e.g. prostate lumens).

The system described in this example solves the drawbacks listed above for automated pathology and other analyses by transforming IR imaging instrumentation using a new concept that combines advances in theory and photonic device technology with spectroscopy. One advantage is the speed of imaging is increased by a factor of ~10 to 100-fold, the spatial resolution will be enhanced 4-fold, and cost will be reduced ~3-fold. Most importantly, for the specific application area focused on here, the approach is entirely compatible with clinical practice and does not require biomedical researchers/clinicians to be re-trained or to perform any expert functions.

In summary, the system described here performs spectroscopy and imaging with an ease that is unmatched by current instruments. This is achieved by a fundamentally different method of recording the data. Hence, one advance is the idea of performing spectroscopy in the manner described and the associated development of hardware to perform the same.

To overcome the performance drawbacks above, the systems and methods described in this example provide an alternative to FT-IR spectroscopy. In contrast with FT-IR spectroscopy in which individual spectral elements are resolved by interferometry, some of the systems and methods described here utilize a large number of narrow bandwidth filters to record spectral elements. A new approach produces precision mid-IR filters from advances in nanofabrication technology, optical modeling and use of unconventional materials for manufacture. Since the recording of data of any spectral element would then be decoupled from recording the entire bandwidth (the FT-IR case), this approach is termed herein discrete frequency IR (DF-IR) spectroscopy.

FIG. 2. Exemplary technology for IR spectroscopy and imaging. FPA stands for focal plane array detector, which is used for imaging, but non-imaging detectors may be used as well.

Compared to FT-IR spectroscopy, there are several advantages to this approach as will be illustrated by specific examples:

1. Instrumentation is considerably simpler and more robust. This is a significant advantage to clinical or research laboratory usage. FT-IR spectroscopy uses a sensitive interferometer and liquid nitrogen cooled detector, whereas the exemplary DF-IR systems described here use a very simple movable part and uncooled detectors.

2. Costs and complexity of instrumentation and operation are lower, as there is no need for an precise interferometer and microscope in the proposed setup 3. In many samples, all data in the IR spectrum is not informative. For tissue, for example, ~35% of recorded data in FT-IR spectroscopy is useful. The rest wastes recording time, storage space and delays information retrieval. Hence, by not recording needless data, the acquisition process can become faster and more efficient.

In one method, an absorption spectrum is obtained by methods that use a discrete set of wavelengths. The constraints for high throughput pathology, however, dictate that the system must ideally be rapid, compact, inexpensive to implement, and provide high illumination intensity over a broad wavelength range (2.5-10.5 µm). One potential alternative, for example, might be to illuminate with a broadband infrared light source through a conventional grating/slit monochromator, where serial adjustment of the monochromator slit position provides output that illuminates the sample one wavelength at a time. While such a method would function in principle, the systems and methods described here enable more rapid and specifically targeted discrete frequency illumination of a biopsy sample. Another approach may be to disperse light on one edge of a 2D camera and record spatial data in a perpendicular direction. This second approach requires the recording of the entire spectrum and cannot record the full image field of view at one time. The approach of this example, described in detail below, utilizes a set of discrete wavelength reflection filters that are used to provide an engineered set of illumination frequencies in rapid succession. This approach has a number of advantages:

a. Efficiency at all wavenumbers is optimized;
b. Frequencies are individually selectable; and
c. Exceptionally large wavelength regions can be covered in a single rotating part.

Using the above advantages, a DF-IR spectroscopy imaging instrument that addresses all the FT-IR imaging shortcomings for tissue imaging is described. One important feature of a DF-IR system is the fabrication and use of a series of mid-IR filters and their incorporation into an imaging system. Major spectroscopic advantages provided by the set of filters are:

1. The ability to provide high reflection efficiency over a narrow wavelength range for each spectral resolution element;

2. A large wavelength range for the entire collection of spectral filters; and

3. The entire set of filters can be produced with a simplified fabrication process, so that all the filters can be produced in parallel with a small number of steps.

The optical filter technology that provides these characteristics is known as a Guided Mode Resonance Filter (GMRF). Operating principles behind GMRFs and their potential use in mid-IR are briefly described next.

GMRF technology. Background. Since their discovery by Wood in 1902 and subsequent analysis, anomalies in periodically modulated structures have attracted much attention. Wang and Magnusson studied in great detail resonant anomalies in waveguide-gratings and showed that structures with a sub-wavelength modulation in refractive index along one-dimension can function as filters that produce complete exchange of energy between forward and backward propagating diffracted waves, with smooth line shapes and arbitrarily low linewidths. This anomalous resonant phenomenon (termed guided-mode resonance) arises due to the introduced periodicity that allows phase-matching of externally incident radiation into modes that can be re-radiated into free-space. Due to the fact that these modes possess finite lifetimes within such structures, they are referred to as 'leaky eigenmodes' of the structures. More recently, guided-mode resonances have been studied and demonstrated in crossed gratings or two-dimensional (2D) PC slabs. The leaky nature of these modes has been successfully exploited towards the development of light emitting diodes (LEDs) with improved extraction efficiency, biosensors and vertically emitting lasers.

Principle of GMRF. Like all optical resonators, GMRFs store energy at the resonance wavelength. This energy is manifested as optical near fields that interact with the device itself as well as with the external environment. Energy is injected into and extracted from the resonant standing waves through phase matching provided by the periodic modulation. In order to understand how the spectral response varies with the sensor design and to maximize the spectral tuning due to changes of the filter design parameters, models have been developed that take as input the device geometry and material parameters, and calculate as output the resulting resonant reflectance response. For normal incidence illumination, the response of the GMRF is coupled to the 2nd order Bragg condition and therefore the spectral location of peak reflection can be given by:

$$\lambda = n_{eff} \Lambda \quad (1)$$

where $\lambda$ is the resonant wavelength, $n_{eff}$ is the effective index and $\Lambda$ is the modulation period. The effective index can be considered a weighted average of the refractive indices of the materials in which the standing wave generated at resonance, referred to as the "resonant mode", is supported. Hence, the large numbers of resonant wavelengths needed for spectroscopy can be readily tailored by changing simple geometric parameters (modulation period). Fabrication of GMRF devices for the mid-IR spectral range, however, presents unique challenges compared to other devices that have spanned ultraviolet ($\lambda$=488 nm), visible ($\lambda$=532 nm and $\lambda$=632 nm), and near-infrared ($\lambda$=860 nm) wavelengths.

Challenges for mid-IR. The primary challenge is the requirement that all the materials of the structure to have little or no absorption at the resonant wavelength in order to maintain near 100% reflection efficiency. Plasma-enhanced chemical vapor deposited (PE-CVD) silicon nitride (SiN) dielectric is utilized specifically for its low level of infrared wavelength absorption, and highly efficient reflectance spectra are observed using these materials. Since there are a large number of frequencies, a secondary challenge is to ensure an efficient manner of both fabrication and use of these filters. Use of a "filter wheel" concept based on a single wafer overcomes this issue. Last, characteristics and uniformity of the filter set must be rapidly and rigorously addressed for spectroscopy. A suite of characterization tools are used for this purpose. One positive aspect of fabricating filters for mid-IR wavelengths is that the device period, which must be less than one-half the resonant wavelength, increases as wavelength increases according to Equation 1. For example, a device designed for a resonant wavelength of $\lambda$=3450 nm, requires a period of $\lambda$=2200 nm with our materials, and devices designed to cover the wavelength range of 250<$\lambda$<3750 nm require a period of 1700<$\lambda$<2580 nm. To produce a linear grating surface structure, the size of etched features will be one half the device period, requiring the photolithographic patterning of lines/spaces with 850<$\lambda$/2<1290 nm. Features of this size are well within the range of dimensions that can be patterned using contact photolithography using conventional photoresists and chrome exposure masks.

Signal to noise comparison with FT-IR. A model of DF-IR major components is compared to the FT-IR case. A broad bandwidth infrared light source illuminates a specially designed optical filter in DF-IR spectroscopy. The filter is designed to only reflect a narrow band of optical wavelengths when illuminated with a broad band of wavelengths. Hence, a bank of filters has to be rotated into position one by one for spectroscopy. For interferometry, a moving mirror provides spectral resolution. The first aspect to note is that the intensity for any wavelength is the same for both cases. Hence, there is no difference in signal to a first approximation. The FT method collects N spectral data points (for example, 2048), with each being measured N times (Fellgett's advantage). The DF-IR approach measures k points (for example, 32), with each being measured once. Hence, for a given data acquisition time, the DF-IR will only be superior in terms of signal to noise ratio (SNR) if $k < \sqrt{N}$. This condition is often met for simple tissue classifications, e.g. for determining epithelial cells from others and cancer/no-cancer problems in breast tissue (e.g. see Table 1).

TABLE 1

Metrics used to separate epithelium from stroma and subsequently used to identify pixels for cancer/no-cancer classification.

| Position (cm$^{-1}$) | Assignment | Molecular Origin |
|---|---|---|
| 1080:1456 | 1080 cm$^{-1}$: symmetric PO$_2^-$ stretching | DNA/RNA |
| | 1456 cm$^{-1}$: asymmetric CH$_3$ bending | Proteins/Lipids |
| 1300-1358 | CH$_2$ wagging | Collagen |
| 1556 | NH bending CH stretching | Protein (Amide II) |
| 1426-1482 | Asymmetric CH$_3$ bending | Proteins/Lipids |
| 1338:1080 | 1338 cm$^{-1}$: CH$_2$ wagging | Collagen |
| | 1080 cm$^{-1}$: symmetric PO$_2^-$ stretching | DNA/RNA |
| 1070-1104 | Symmetric PO$_2^-$ stretching | DNA/RNA |
| 1080:1234 | 1080 cm$^{-1}$: symmetric PO$_2^-$ stretching | DNA/RNA |
| | 1234 cm$^{-1}$: NH bending, CH stretching, CH$_2$ wagging | Protein (Amide III) |
| 1324-1358 | CH$_2$ wagging | Collagen |

In an actual data acquisition, however, the acquisition time is not fixed. Instead, the SNR for a given signal is fixed. In this regard, DF-IR promises superiority due to the nature of detection. For a given signal, FT-IR encodes the intensity in time such that there is a massive signal around zero optical retardation, which dies out quickly. The spectral SNR is the SNR of this central signal divided by $\sqrt{N}$. For a given source, if N is large, SNR suffers. To cover the bandwidth over which peaks are used, N is typically of the order of 512-2048 points. For an ideal detector, this would not be a problem. The analog to digital converters (ADC) for detectors, however, are usually no more than 16 bits. Hence the full dynamic range of the interferogram has to fit into 15 bits. Further, the thermal background occupies some signal and the full range is often not utilized for fear of saturating the detector. Noise is often 2 bits for cooled and 5 bits (D* is ~10 fold smaller) for uncooled FPA detectors. Consequently, for one scan, a pixel's SNR is no more than 250:1 for FT-IR imaging. Typically, studies cooled detectors report a SNR of about 100:1 and uncooled detectors report a SNR of about 10:1. Hence, even though a cooled 128×128 FPA is much more costly to implement than an uncooled 320×240 bolometer FPA, no uncooled FPA based FT-IR systems are available because of the poor SNR.

Methods such as gain ranging, staggered step-scan, usual and interleaved rapid scan, interferometer modulation and detector gating have been proposed to raise the SNR. The biggest jumps, however, have come from expensive new detectors or a trade-off in using very small detectors (16×1). While small detectors provide impressive SNRs, spatial coverage suffers dramatically. One is actually better off scanning a 256×256 detector 1024 times than scan the same with a 16×1 detector. Progress is limited by our inability to keep improving hardware or inventing new acquisition schemes.

For DF-IR, the situation is simplified. The dynamic range is filled by the signal and the SNR can be 1000:1 (cooled FPA) or 100:1 (uncooled FPA). Further, the ADC can be filled by integrating the signal for varying times at each filter setting. Hence, uniform SNRs (or by design, enhanced SNRs at any frequency) are obtained by software control. This opportunity for control is not available in FT-IR. Last, array detectors are much larger. Hence, coverage can be enhanced and more time can be spent co-averaging signal to improve SNR. Thus, the DF-IR approach is not only simpler, more robust and cheaper, but is actually provides enhanced performance.

Fabrication of mid-IR GMRF and characterization for use in spectroscopy. FIG. 3. (A) Schematic cross section diagram of the GMRF filter structure. (B) Top view microscope image of the edge of an etched GMRF grating. (C) Atomic force microscope image of the fabricated GMRF structure showing the grating depth and period, and D. Photograph of a completed GMRF filter wheel.

GMRFs are fabricated using the design similar to that shown in FIG. 3. The device is comprised of a low refractive index substrate (soda lime glass, n=1.5) upon which a thin film of high refractive dielectric material (silicon nitride, n=1.975) is deposited. Photolithography is used to define a 1-dimensional linear grating pattern upon the dielectric material, and a reactive ion etch process is used to etch grooves partially into its surface. With correct selection of the material refractive index parameters, dielectric layer thickness, and grating depth, the device structure shown in FIG. 3 performs the function of a highly efficient reflectance filter at the resonant wavelength. At the resonant wavelength, the structure achieves up to 95-100% reflection efficiency, while all other wavelengths are transmitted to be eventually absorbed by the thick soda glass. A Rigorous Coupled Wave Analysis (RCWA) computer simulation of the reflection efficiency as a function of wavelength is shown in FIG. 5A for a representative structure ($t_{SiN}$=600 nm, $d_{grating}$=300 nm, $\lambda$=2200 nm). Up to 100% reflection efficiency is theoretically predicted, with a reflection bandwidth of 50-100 nm full-width-at-half-maximum (FWHM) in this case. The efficiency and FWHM depend both on the optical alignment as well as properties of the underlying materials. The resonant reflection shown in FIG. 5A assumes that the incident illumination is polarized with the electric field parallel to the grating lines (TE mode). Therefore, some systems incorporate a linear polarizing filter in the path between the infrared light source and the sample for maximum efficiency.

Figure 5:
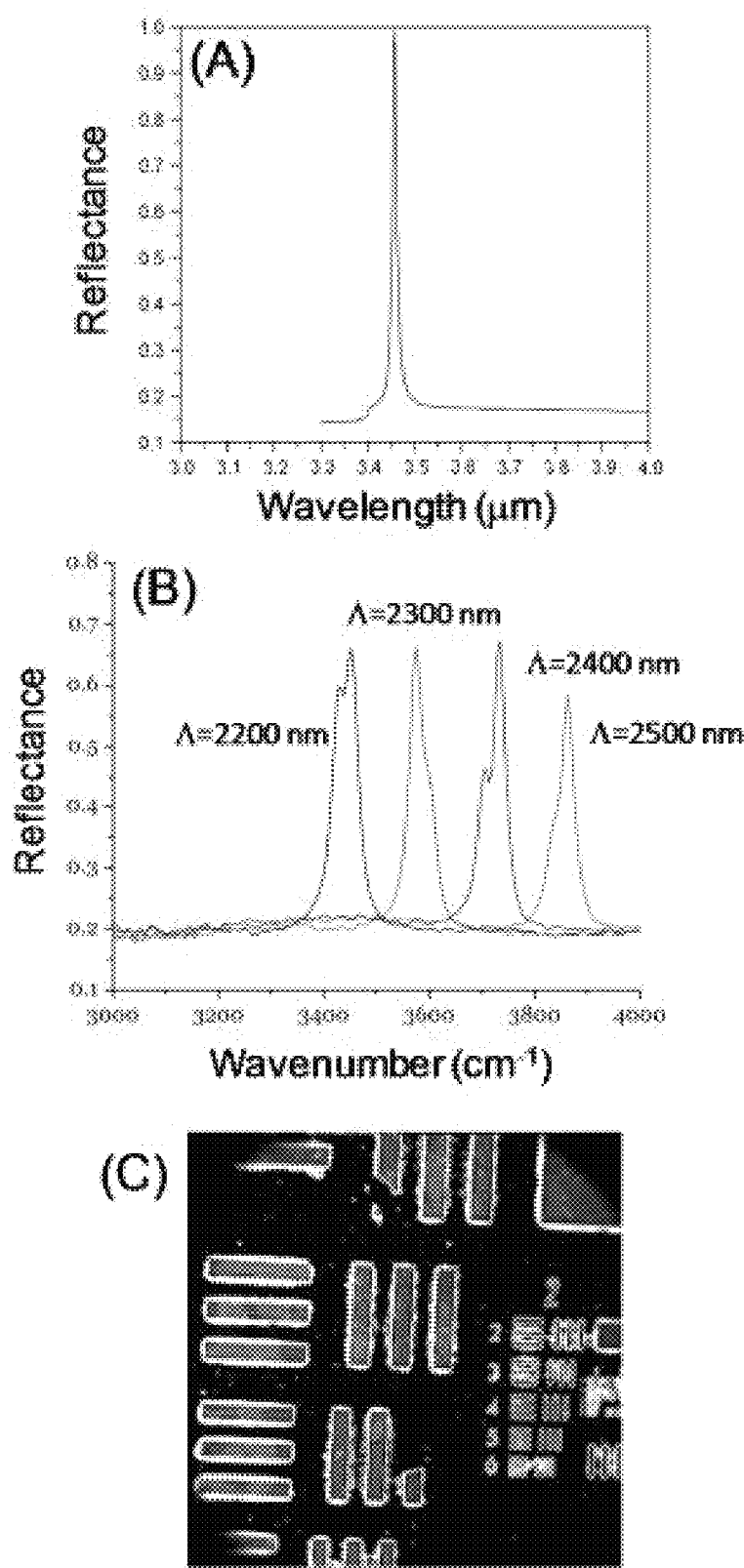
FIGS. 5A and 5B show reflectances of a number of GMRFs.
FIG. 5C shows an infrared absorption image of patterned SU-8.

FIG. 5. RCWA computer simulation of the reflectance spectrum of a GMRF structure ($\lambda$=2200 nm, $t_{SiN}$=600 nm, $d_{grating}$=300 nm). (B) Measured reflectance spectra from devices fabricated together on a single glass substrate with $t_{SiN}$=600 nm, $d_{grating}$=300 nm, but four slightly different periods. The four filters were fabricated on the same substrate and encompass an absorption band of the SU-8 resin. (C) The image of the OH stretching absorption band (~3455 cm$^{-1}$) of a USAF1951 target made from SU-8 resin on a glass slide.

Preliminary experiments were performed to validate the performance of a small set of GMRF filters for shorter wavelengths in the mid-IR, and to demonstrate the ability to fabricate filters over a broad wavelength range with a single dielectric thin film and a single photolithography process. In order to obtain reflectance filters for different wavelengths, the period (Λ) of the structure is adjusted, while the dielectric film thickness and etch depth remain unchanged. In this way, a fabrication process using one dielectric thin film and a single etch process can produce highly efficient filters that cover a broad band of wavelengths. Using the fabrication method described above, 4 GMRFs were fabricated upon a single glass substrate with device parameters ($t_{SiN}$=600 nm, $d_{grating}$=300 nm, λ=2200, 2300, 2400, and 2500 nm). The resulting devices displayed the reflection spectra (actually obtained by measuring transmission efficiency as a function of wavelength, and then inverting the data for consistency with the simulation) shown in FIG. 5B. These preliminary results clearly demonstrate that efficient narrowband reflectance filters can be produced at mid-IR wavelengths, with reflected wavelengths that are tunable by adjustment of the device period. A preliminary image at a single wavenumber shows the potential of the technology.

FIG. 4B. Photo of filter wheel. The squares are individual GMRF filters.

To enable scanning at more frequencies, single filters on single substrates are not useful. Hence, a "filter wheel" is utilized in which many filters are fabricated all at once and are separated by being spatially arranged in a ring. Any frequency can hence, be addressed rapidly and randomly by simply turning the wheel. A filter wheel was designed, fabricated, and characterized for its optical properties (FIG. 4B).

FIG. 6. Schematic for obtaining narrowband light from a broadband source.

To use the filter wheel: first, the GMRFs are characterized in a convenient and consistent manner. Second, their performance in a system comparable to FT-IR imaging systems is evaluated. A modular approach is used to tackle both issues. The setup consists of a "source" component that includes the IR source, various optics to condense and guide the beam and a multi-frequency GMRF. Second, this spectrally-resolved source is then interfaced to a commercial FT-IR spectrometer (for characterization) and separately to a commercially available microscope (for comparison with FT-IR imaging).

A schematic of the setup is shown in FIG. 6. The infrared emitter (Newport 6363) is housed along with a reflector assembly (60100 Phootmax Housing), collimating optics and an aperture to obtain a collimated beam (broadband source). The 3 inch beam is condensed to 5 mm using symmetrical parabolic mirrors and is optionally passed through an aperture or polarizer, if required. A 50:50 beamsplitter (BS) (Ge on $BaF_2$) directs half the beam to a rotatable GMRF filter bank. The bank of GMRF filters is configured spatially with nanostructured regions that reflect specific spectral bands in a collimated beam of incident IR radiation. A notch (black line) denotes the starting/end point of rotation and is used to automatically align the filter bank in conjunction with the stepper motor. An inexpensive He—Ne laser and diode detector is used to monitor the position of the notch in software such that the source module is always producing the frequency dictated by software. The stepper motor is controlled by software to rotate the wheel and custom mount to sequentially scan a specified bandwidth or randomly access any frequency desired. A spectrally narrowband beam is reflected back and is transmitted for use in a commercial interferometer (Bruker Vertex 70) or an IR microscope (Varian UMA 600). The first transmitted beam at BS is absorbed to prevent stray light while half the returning beam from the filter that is reflected goes back to the source (not shown).

The filter wheel is comprised of a series of GMRFs arranged in a circular pattern, where each filter region in the series is designed to reflect only one wavelength within the specified wavelength range. The reflected wavelengths is selected to be uniform over a bandwidth or is designed to coincide with the absorption wavelength of biomarkers of greatest interest, as well as some wavelengths in between the target wavelengths for background correction. Rotation of the filter wheel so that each individual region may be illuminated in series results in illumination of the test sample only at the designed wavelengths of interest. By capturing a series of images at each wavelength with an FPA detector, the system performs discrete frequency absorption spectroscopic imaging.

References

E. N. Lewis, P. J. Treado, R. C. Reeder, G. M. Story, A. E. Dowrey, C. Marcott, and I. W. Levin, "Fourier transform spectroscopic imaging using an infrared focal-plane array detector," Anal Chem, vol. 67, pp. 3377-81, Oct. 1, 1995.

R. Bhargava and I. W. Levin, Spectrochemical Analysis Using Infrared Multichannel Detectors Wiley-Blackwell, 2005.

I. W. Levin and R. Bhargava, "Fourier transform infrared vibrational spectroscopic imaging: integrating microscopy and molecular recognition," Annu Rev Phys Chem, vol. 56, pp. 429-74, 2005.

G. Srinivasan and R. Bhargava, "Fourier transform-infrared spectroscopic imaging: The emerging evolution from a microscopy tool to a cancer imaging modality," Spectroscopy, vol. 22, pp. 30-+, July 2007.

M. Diem, P. R. Griffiths, and J. M. Chalmers, Vibrational Spectroscopy for Medical Diagnosis Wiley, 2008.

R. Bhargava and I. W. Levin, "Fourier transform infrared imaging: theory and practice," Anal Chem, vol. 73, pp. 5157-67, Nov. 1, 2001.

R. W. Wood, "On a remarkable case of uneven distribution of light in a diffraction grating spectrum," Philos. Mag., vol. 4, pp. 392-402, 1902.

L. Rayleigh, "On the dynamical theory of gratings," Proc. R. Soc. London Ser. A, vol. 79, pp. 399-416, 1907.

A. Hessel and A. A. Oliner, "A new theory of Wood's anomalies on optical gratings," Appl. Opt., vol. 4, pp. 1275-1297, 1965.

E. Popov, L. Mashev, and D. Maystre, "Theoretical study of the anomalies of coated dielectric gratings," Opt. Acta, vol. 33, pp. 607-619, 1986.

H. L. Bertoni, L. H. S. Cheo, and T. Tamir, "Frequency selective reflection and transmission by a periodic dielectric layer," IEEE Trans. Antennas Propag., vol. 37, pp. 78-83, 1989.

S. S. Wang, R. Magnusson, and J. S. Bagby, "Guided-mode resonances in planar dielectric-layer diffraction gratings," J. Opt. Soc. Am. A, vol. 7, pp. 1470-1474, 1990.

R. Magnusson and S. S. Wang, "New principle for optical filters," Appl. Phys. Lett., vol. 61, pp. 1022-1024, 1992.

S. S. Wang and R. Magnusson, "Theory and applications of guided-mode resonance filters," Appl. Opt., vol. 32, pp. 2606-2613, 1993.

S. Peng and G. M. Morris, "Resonant scattering from two-dimensional gratings," J. Opt. Soc. Am. A, vol. 13, pp. 993-1005, 1996.

S. Peng and G. M. Morris, "Experimental demonstration of resonant anomalies in diffraction from two-dimensional gratings," Opt. Lett., vol. 21, pp. 549-551, 1996.

S. Boonruang, A. Greenwell, and M. G. Moharam, "Multiline two-dimensional guided-mode resonant filters," Appl. Opt., vol. 45, pp. 5740-5747 2006.

W. Suh and S. Fan, "All-pass transmission or flattop reflection filters using a single photonic crystal slab," Appl. Phys. Lett., vol. 84, pp. 4905-4907, 2004.

A. Rosenberg, M. Carter, J. Casey, M. Kim, R. Holm, R. Henry, C. Eddy, V. Shamamian, K. Bussmann, S. Shi, and D. Prather, "Guided resonances in asymmetrical GaN photonic crystal slabs observed in the visible spectrum," Opt. Express, vol. 13, pp. 6564-6571, 2005.

S. Fan and J. D. Joannopoulos, "Analysis of guided resonannces in photonic crystal slabs," Phys. Rev. B, vol. 65, pp. 235112-1-235112-8, 2002.

V. N. Astratov, I. S. Culshaw, R. M. Stevenson, D. M. Whittaker, M. S. Skolnick, T. F. Krauss, and R. M. D. L. Rue, "Resonant Coupling of Near-Infrared Radiation to Photonic Band Structure Waveguides," J. Lightwave Technol., vol. 17, 1999, (2050-2057).

M. Boroditsky, T. F. Krauss, R. Coccioli, R. Vrijen, R. Bhat, and E. Yablonovitch, "Light extraction from optically pumped light-emitting diode by thin-slab photonic crystals," Appl. Phys. Lett., vol. 75, 1999, (1036-1038).

M. Boroditsky, R. Vrijen, T. F. Krauss, R. Coccioli, R. Bhat, and E. Yablonovitch, "Spontaneous Emission Extraction and Purcell Enhancement from Thin-Film 2-D Photonic Crystals," J. Lightwave Technol., vol. 17, pp. 2096-2112, 1999.

A. A. Erchak, D. J. Ripin, S. Fan, P. Rakich, J. D. Joannopoulos, E. P. Ippen, G. S. Petrich, and L. A. Kolodziejski, "Enhanced coupling to vertical radiation using a two-dimensional photonic crystal in a semiconductor light-emitting diode," Appl. Phys. Lett., vol. 78, 2001, (563-565).

B. Cunningham, B. Lin, J. Qiu, P. Li, J. Pepper, and B. Hugh, "A plastic colorimetric resonant optical biosensor for multiparallel detection of label-free biochemical interactions," Sens. Act. B, vol. 81, pp. 316-328, 2002.

T. Kobayashi, Y. Kanamori, and K. Hane, "Surface laser emission from solid polymer dye in a guided mode resonant grating filter structure," Appl. Phys. Lett., vol. 87, p. 151106, 2005.

I. D. Block, N. Ganesh, M. Lu, and B. T. Cunningham, "A sensitivity model for predicting photonic crystal biosensor performance," IEEE Sensors Journal, vol. 8, pp. 274-280, 2008.

S. Peng, "Experimental demonstration of resonant anomalies in diffraction from two-dimensional gratings," Optics Letters, vol. 21, pp. 549-551, G. Michael Morris.

N. Ganesh, I. D. Block, and B. T. Cunningham, "Near UV-wavelength photonic crystal biosensor with enhanced surface-to-bulk sensitivity ratio," Applied Physics Letters, vol. 89, pp. 023901-023904, 2006.

D. Dobbs and B. T. Cunningham, "Optically tunable photonic crystal reflectance filters," Applied Optics, vol. 45, pp. 7286-7293, 2006.

F. Yang, G. Yen, and B. T. Cunningham, "A voltage-tuned resonant reflectance optical filter for visible wavelengths fabricated by nanoreplia molding," Applied Physics Letters, vol. 90, pp. 261109-261111, 2007.

B. T. Cunningham, P. Li, B. Lin, and J. Pepper, "Colorimetric resonant reflection as a direct biochemical assay technique," Sensors and Actuators B, vol. 81, pp. 316-328, 2002.

B. T. Cunningham, J. Qiu, P. Li, J. Pepper, and B. Hugh, "A plastic colorimetric resonant optical biosensor for multiparallel detection of label-free biochemical interactions," Sensors and Actuators B, vol. 85, pp. 219-226, 2002.

R. Bhargava and I. W. Levin, "Effective time averaging of multiplexed measurements: a critical analysis," Anal Chem, vol. 74, pp. 1429-35, Mar. 15, 2002.

A. S. Haka, I. W. Levin, and E. N. Lewis, "Uncooled barium strontium titanium focal plane array detection for mid-infrared Fourier transform spectroscopic imaging," Appl Spectrosc, vol. 54, pp. 753-755, May 2000.

Committee on Revealing Chemistry through Advanced Chemical Imaging, National Research Council Visualizing Chemistry: The Progress and Promise of Advanced Chemical Imaging 2006: National academies press.

Puppels, G. J., De Mul, F. F. M., Otto, C., Greve, J., Robert-Nicoud, M., Arndt-Jovin, D. J., Jovin, T. M. Studying single living cells and chromosomes by confocal Raman microspectroscopy. Nature 347, 301-303 (1990).

Colarusso, P., Kidder, L. H., Levin, I. W., Fraser, J. C., Arens, J. F., Lewis, E. N. Infrared spectroscopic imaging: From planetary to cellular systems. Appl. Spectrosc. 52, 106a-120a (1998).

Ellis D I, Goodacre R. Metabolic fingerprinting in disease diagnosis: biomedical applications of infrared and Raman spectroscopy. Analyst 131, 875-885 (2006).

Bhargava, R. Practical FTIR chemical imaging for cancer pathology. Anal Bioanal Chem. 2008 389(1155-1169).

Koenig J L, Wang S Q, Bhargava R. FT-IR Images Anal. Chem. 73, 360A-369A (2001).

Reddy, R. K. Bhargava, R. A framework to predict accuracy and statistical validity of automated histologic classification results from chemical imaging. Submitted 2009.

Alivisatos, P. The use of nanocrystals in biological detection. Nat. Biotechnol. 22, 47-52 (2004).

Krafft, C., Steiner, G., Beleites, C. Disease recognition by infrared and Raman spectroscopy. J. Biophotonics 2, 13-28 (2009).

Uzunbajakava, N., Lenferink, A., Kraan, Y., Volokhina, E., Vrensen, G., Greve, J., Otto, C. Nonresonant confocal Raman imaging of DNA and protein distribution in apoptotic cells. Biophys. J. 84, 3968-3981 (2003).

Swain, R. J., Stevens, M. M. Raman microspectroscopy for non-invasive biochemical analysis of single cells. Biochemical Society Transactions 35, 544-549 (2007).

Volkmer, A. Vibrational imaging and microspectroscopies based on coherent anti-stokes raman scattering microscopy. J. Physics D: Applied Physics 38, R59-R81 (2005).

Cheng, J.-X., Jia, Y. K., Zheng, G., Xie, X. S. Laser-scanning coherent anti-Stokes Raman scattering microscopy and applications to cell biology. Biophys. J. 83, 502-509 (2002).

Kano, H., Hamaguchi, H.-O. Vibrationally resonant imaging of a single living cell by supercontinuum-based multiplex coherent anti-Stokes Raman scattering microspectroscopy Opt. Exp. 13, 1322-1327 (2005).

Willets, K. A. Surface-enhanced Raman scattering (SERS) for probing internal cellular structure and dynamics. Anal Bioanal. Chem. 394, 85-94 (2009).

Braue Jr., Ernest H., Pannella, Michael G. consistency in circle cell FT-IR analysis of aqueous solutions. Appl. Spectrosc. 41, 1057-1067 (1987).

Chan, J., Fore, S., Wachsmann-Hogiu, S., Huser, T. Raman spectroscopy and microscopy of individual cells and cellular components. Laser and Photonics Reviews 2, 325-349 (2008).

Snively, C. M., Katzenberger, S., Oskarsdottir, G., Lauterbach, J. Fourier-transform infrared imaging using a rapid-scan spectrometer. Opt. Lett. 24, 1841-1843 (1999).

Bhargava R and Levin I W, eds., Spectrochemical Analysis Using Infrared Multichannel Detectors, Blackwell Publishing, pp. 56-84, Oxford (2005).

Biochimica et Biophysica Acta-Biomembranes, special issue, volume 1758, 2006.

Haaland, D. M., Jones, R. D. T., Thomas, E. V. Multivariate classification of the infrared spectra of cell and tissue samples. Appl. Spectrosc. 51, 340-345 (1997).

Diem M, Romeo M, Boydston-White S, Miljkovic M, Matthaus C A decade of vibrational micro-spectroscopy of human cells and tissue (1994-2004) Analyst 129, 880-885 (2004).

M Jackson From biomolecules to biodiagnostics: Spectroscopy does it all. Faraday Discuss. 126, 1-18 (2004).

Andrus, P. G. Cancer monitoring by FTIR spectroscopy. Tech. Cancer Res. Treat. 5, 157-167 (2006).

Olumi, A. F., Grossfeld, G. D., Hayward, S. W., Carroll, P. R., Tlsty, T. D., Cunha, G. R. Carcinoma-associated fibroblasts direct tumor progression of initiated human prostatic epithelium. Cancer Res. 59, 5002-5011 (1999).

Goodpaster T, Legesse-Miller A, Hameed M R, Aisner S C, Randolph-Habecker J, Coller H A. J Histochem Cytochem. An immunohistochemical method for identifying fibroblasts in formalin-fixed, paraffin-embedded tissue. 56, 347-58 (2008).

Keith, F. N. Bhargava, R. Two class models for Automated Breast Histopathology Using Mid-IR Spectroscopic Imaging. Submitted. 2009.

Fernandez D C, Bhargava R, Hewitt S M, Levin I W. Infrared spectroscopic imaging for histopathologic recognition. Nat Biotechnol. 23, 469-474 (2005).

Diem, M., Chiriboga, L., Lasch, P., Pacifico, A. IR spectra and IR spectral maps of individual normal and cancerous cells. Biopolymers—Biospectroscopy Section 67, 349-353 (2002).

Lasch, P., Pacifico, A., Diem, M. Spatially resolved IR microspectroscopy of single cells. Biopolymers—Biospectroscopy Section 67, 335-338 (2002).

Cohenford, M. A., Rigas, B. Cytologically normal cells from neoplastic cervical samples display extensive structural abnormalities on IR spectroscopy: Implications for tumor biology. Proc. Natl. Acad. Sci. USA 95, 15327-15332 (1998).

Wood, B. R., Chiriboga, L., Yee, H., Quinn, M. A., McNaughton, D., Diem, M. Fourier transform infrared (FTIR) spectral mapping of the cervical transformation zone, and dysplastic squamous epithelium. Gynecologic Oncology 93, 59-68 (2004).

Argov, S., Ramesh, J., Salman, A., Sinelnikov, I., Goldstein, J., Guterman, H., Mordechai, S. Diagnostic potential of Fourier-transform infrared microspectroscopy and advanced computational methods in colon cancer patients J. Biomed. Opt. 7, 248-254 (2002).

Wood, B. R., Quinn, M. A., Tait, B., Ashdown, M., Hislop, T., Romeo, M., McNaughton, D. FTIR microspectroscopic study of cell types and potential confounding variables in screening for cervical malignancies. Biospectroscopy 4, 75-91 (1998).

S. Boydston-White, T. Gopen, S. Houser, J. Bargonetti and M. Diem, Biospectroscopy 5 (1999).

Kuimova, M. K., Chan, K. L. A., Kazarian, S. G. Chemical imaging of live cancer cells in the natural aqueous environment. Appl. Spectrosc. 63, 164-171 (2009).

Moss, D. A., Keese, M., Pepperkok, R. IR microspectroscopy of live cells. Vib. Spectrosc. 38, 185-191 (2005).

Timlin, J. A., Martin, L. E., Lyons, C. R., Hjelle, B., Alam, M. K. Dynamics of cellular activation as revealed by attenuated total reflectance infrared spectroscopy Vibrational Spectroscopy, Article in Press (2008).

Holman, H.-Y. N., Martin, M. C., McKinney, W. R. Tracking chemical changes in a live cell: Biomedical applications of SR-FTIR spectromicroscopy Spectroscopy 17, 139-159 (2003).

Edwards, G. S., Hutson, M. S. Advantage of the Mark-III FEL for biophysical research and biomedical applications. Journal of Synchrotron Radiation 10, 354-357 (2003).

Charlton, C., Katzir, A., Mizaikoff, B. Infrared evanescent field sensing with quantum cascade lasers and planar silver halide waveguides, Analytical Chemistry 77, 4398-4403 (2005).

Hvozdara, L., Pennington, N., Kraft, M., Karlowatz, M., Mizaikoff, B. Quantum cascade lasers for midinfrared spectroscopy Vibrational Spectroscopy 30, 53-58 (2002).

David A. Moss, Michael Keese, Rainer Pepperkok, IR microspectroscopy of live cells, Vibrational Spectroscopy, Volume 38, Issues 1-2, A Collection of Papers Presented at the 3rd International Conference "Shedding Light on Disease: Optical Diagnostics for the New Millenium (SPEC 2004", Newark, N.J., USA, 19-23 Jun. 2004. Dedicated to Professor Henry Mantsch, 29 Jul. 2005, Pages 185-191, ISSN 0924-2031, DOI: 10.1016/j.vibspec.2005.04.004.

Griffiths, P. R.; De Haseth, J. A. Fourier Transform Infrared Spectrometry. (2nd edn), John Wiley & Sons: New York, USA, 1986.

Bhargava R, Fernandez D C, Schaeberle M D, Levin I W. "Theory and application of gain ranging to Fourier transform infrared spectroscopic imaging." Appl. Spectrosc. 55, 1580-1589, 2001.

Bhargava R, Schaeberle M D, Fernandez D C, Levin I W. "Novel route to faster Fourier transform infrared spectroscopic imaging." Appl. Spectrosc. 55, 1079-1084, 2001.

Huffman S W, Bhargava R, Levin I W. "Generalized implementation of rapid-scan Fourier transform infrared spectroscopic imaging." Appl. Spectrosc. 56: 965-969, 2002.

Bhargava R, Levin I W. "Time-resolved Fourier transform infrared spectroscopic imaging." Appl. Spectrosc. 57: 357-366, 2003.

Bhargava R, Wang S Q, Koenig J L. "FTIR microspectroscopy of polymeric systems." Adv. Polym. Sci. 163: 137-191, 2003.

Bhargava R, Fernandez D C, Hewitt S M, Levin I W. "High throughput assessment of cells and tissues: Bayesian classification of spectral metrics from infrared vibrational spectroscopic imaging data." Biochim Biophys Acta. 1758(7): 830-845, 2006.

Webb A R. Statistical Pattern Recognition (John Wiley & Sons, New York, 2002).

Simon R, Radmacher M D, Dobbin K, McShane L M. Pitfalls in the use of DNA microarray data for diagnostic and prognostic classification. J Natl Cancer Inst. 95:14-18 (2003).

Ransohoff D F. Challenges and opportunities in evaluating diagnostic tests. J Clin Epidemiol. 55:1178-1182 (2002).

Conrads T P, Zhou M, Petricoin E F III, Liotta L A, Veenstra T D. Cancer diagnosis using proteomic patterns Expert Rev. Mol. Diagn. 3: 411-420 (2003).

Alaiya A, Al-Mohanna M, Linder S Clinical Cancer Proteomics: Promises and Pitfalls J. Proteome Res. 4: 1213-1222 (2005).

Ransohoff, D. F. Rules of evidence for cancer molecular-marker discovery and validation. Nature Reviews Cancer 4, 309-314 (2004).

Ransohoff, D. F. The process to discover and develop biomarkers for cancer: A work in progress. Journal of the National Cancer Institute 100, 1419-1420 (2008).

Hoist, G. C., Testing and Evaluation of Infrared Imaging Systems 1998: SPIE.

Bhargava R, Wang S Q, Koenig J L. "Route to higher fidelity FT-IR imaging." Appl. Spectrosc. 54: 486-495, 2000.

Bhargava, R., Fernandez, D. C., Hewitt, S. M., Levin, I. W. High throughput assessment of cells and tissues: Bayesian classification of spectral metrics from infrared vibrational spectroscopic imaging data. Biochim Biophys Acta. 2006 1758(7):830-45.

Christiansen, G. S., Danes, B., Allen, L., and Leinfelder, P. J., A culture chamber for the continuous biochemical and morphological study of living cells in tissue culture, Experimental Cell Research 5: 10-15 (1953).

Biospectroscopy, 1, 37-45, 1995.
Biochimica et Biophysica Acta, 1270, 1-6, 1995.
Cancer Det. Prevent., 23(3), 245-253, 1999.
Appl. Spectrosc. Rev., 36(2-3), 239-298, 2001.

Statements Regarding Incorporation by Reference and Variations

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups and classes that can be formed using the substituents are disclosed separately. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of materials are intended to be exemplary, as it is known that one of ordinary skill in the art can name the same material differently. One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A spectrometer comprising:
   a source for generating a beam of electromagnetic radiation;
   one or more wavelength-selective filters, wherein the one or more wavelength-selective filters comprise guided mode resonance filters and wherein at least one wavelength-selective filter is positioned in optical communication with the source; and
   a detector for detecting electromagnetic radiation, the detector positioned in optical communication with at least one wavelength-selective filter.

2. The spectrometer of claim 1, further comprising a sample chamber positioned in optical communication with at least one wavelength-selective filter.

3. The spectrometer of claim 2, wherein the sample chamber is positioned in optical communication with the source.

4. The spectrometer of claim 2, wherein the sample chamber is positioned in optical communication with the detector.

5. The spectrometer of claim 1, further comprising one or more additional wavelength-selective filters selected from the group consisting of: a reflective optical filter, a transmissive optical filter, a guided mode resonance filter, a distributed Bragg reflective filter and any combination of these.

6. The spectrometer of claim 1, wherein at least one of the one or more wavelength-selective filters has a reflectance linewidth selected over the range of 2 $cm^{-1}$ to 128 $cm^{-1}$.

7. The spectrometer of claim 1, wherein at least one of the one or more wavelength-selective filters has a maximum reflectance selected over the range of 10% to 100%.

8. The spectrometer of claim 1, wherein at least one of the one or more wavelength-selective filters has a reflectance contrast greater than 100 or selected over the range of 10 to 1000000.

9. The spectrometer of claim 1, wherein at least one of the one or more wavelength-selective filters has a reflectance band center position selected over the range of 0.2 µm to 14 µm.

10. The spectrometer of claim 9, wherein at least one of the one or more wavelength-selective filters has a reflectance band center position selected from the group consisting of 1080 $cm^{-1}$, 1456 $cm^{-1}$, 1556 $cm^{-1}$, 1338 $cm^{-1}$ and 1234 $cm^{-}$.

11. The spectrometer of claim 9, wherein at least one of the one or more wavelength-selective filters has a reflectance band center position selected over the range of 900 to 1975 $cm^{-1}$, 1300 to 1358 $cm^{-1}$, 1426 to 1482 $cm^{-1}$, 1070 to 1104 $cm^{-1}$ or 1324 to 1358 $cm^{-1}$.

12. The spectrometer of claim 1, wherein the one or more wavelength-selective filters are located on a filter wheel, the filter wheel configured to position one wavelength-selective filter at a time in optical communication with the source.

13. The spectrometer of claim 12, wherein the one or more wavelength-selective filters are sequentially positioned in optical communication with the source.

14. The spectrometer of claim 1, further comprising one or more optical elements positioned in optical communication with the source.

15. The spectrometer of claim 14, wherein the one or more optical elements are selected from the group consisting of: polarizers, mirrors, apertures, lenses, prisms, windows, filters and any combination of these.

16. The spectrometer of claim 1, wherein the spectrometer is an imaging spectrometer and the detector is an array detector.

17. The spectrometer in claim 1, wherein the detector is a single element detector.

18. The spectrometer of claim 1, wherein the detector is a cooled detector.

19. The spectrometer of claim 1, wherein at least one of the wavelength-selective filters comprises a multilayered structure that is spatially varying in one or more dimensions.

20. The spectrometer of claim 1, wherein at least one of the one or more wavelength-selective filters comprises:
a substrate having a first index of refraction; and
a dielectric layer having a second index of refraction disposed over at least a portion of the substrate, wherein the dielectric layer has a periodic thickness.

21. The spectrometer of claim 20, wherein the dielectric layer has a periodicity selected over the range of 1000 nm to 6000 nm.

22. The spectrometer of claim 20, wherein the dielectric layer has a first thickness selected over the range of 100 nm to 500 nm and a second thickness selected over the range of 200 nm to 1000 nm.

23. The spectrometer of claim 20, wherein the filter substrate comprises a material selected from the group consisting of: soda lime glass, germanium, silicon and any combination of these.

24. The spectrometer of claim 20, wherein the dielectric layer comprises a material which does not substantially absorb infrared electromagnetic radiation.

25. The spectrometer of claim 20, wherein the dielectric layer comprises silicon nitride.

26. A method of measuring an electromagnetic spectral response of a sample, the method comprising the steps of:
generating a beam of electromagnetic radiation;
directing the beam of electromagnetic radiation onto a wavelength-selective filter comprising a guided mode resonance filter, thereby generating a beam of filtered electromagnetic radiation;
directing the beam of filtered electromagnetic radiation through the sample, thereby exposing the sample to filtered electromagnetic radiation; and
detecting filtered electromagnetic radiation which interacts with the sample.

27. A method of measuring an electromagnetic spectral image, the method comprising the steps of:
generating a beam of electromagnetic radiation;
directing the beam of electromagnetic radiation onto a wavelength-selective filter comprising a guided mode resonance filter, thereby generating a beam of filtered electromagnetic radiation;
directing the beam of filtered electromagnetic radiation into a microscope, wherein the microscope focuses the filtered electromagnetic radiation;
providing a sample in the microscope, thereby exposing the sample to focused filtered electromagnetic radiation; and
imaging the focused filtered electromagnetic radiation onto a two dimensional detector.

28. A method of measuring an absorbance image, the method comprising the steps of:
generating a beam of electromagnetic radiation;
directing the beam of electromagnetic radiation into a microscope, wherein the microscope focuses the electromagnetic radiation;
providing a sample in the microscope, thereby exposing the sample to a beam of focused electromagnetic radiation;
directing the beam of focused electromagnetic radiation onto a wavelength-selective filter comprising a guided mode resonance filter, thereby generating filtered electromagnetic radiation; and
imaging the filtered electromagnetic radiation onto a two dimensional detector.

29. The method of claim 28, wherein the beam of electromagnetic radiation comprises infrared electromagnetic radiation.

30. The method of claim 28, wherein the two dimensional detector comprises a two dimensional infrared detector.

31. The spectrometer of claim 1, wherein each of said guided mode resonance filters independently has a reflectance band center position in the mid-infrared spectral region and wherein said detector is for detecting said electromagnetic radiation in the mid-infrared spectral region.

32. The method of claim 26 wherein said guided mode resonance filter has a reflectance band center position in the mid-infrared spectral region, thereby generating said filtered electromagnetic radiation in the mid-infrared spectral region.

* * * * *

UNITED STATES PATENT AND TRADEMARK OFFICE
CERTIFICATE OF CORRECTION

PATENT NO. : 8,593,630 B2  
APPLICATION NO. : 12/900172  
DATED : November 26, 2013  
INVENTOR(S) : Rohit Bhargava and Brian T. Cunningham Page 1 of 1

It is certified that error appears in the above-identified patent and that said Letters Patent is hereby corrected as shown below:

In the Claims:

In claim 10, column 22, line 67, replace "1234 cm" with --1234 $cm^{-1}$--.

Signed and Sealed this
Eighteenth Day of March, 2014

Michelle K. Lee
*Deputy Director of the United States Patent and Trademark Office*